US009789177B2

(12) United States Patent
O'Hehir et al.

(10) Patent No.: US 9,789,177 B2
(45) Date of Patent: Oct. 17, 2017

(54) IMMUNOGENIC PROTEIN PAS N 1 FROM BAHIA GRASS POLLEN

(71) Applicant: The University of Queensland, Brisbane (AU)

(72) Inventors: Robyn O'Hehir, Melbourne (AU); Janet Davies, Woolloongabba (AU); Jennifer Rolland, Melbourne (AU)

(73) Assignee: Queensland University of Technology, Brisbane (AU)

( * ) Notice: Subject to any disclaimer, the term of this patent is extended or adjusted under 35 U.S.C. 154(b) by 0 days.

(21) Appl. No.: 14/311,944

(22) Filed: Jun. 23, 2014

(65) Prior Publication Data

US 2014/0302073 A1    Oct. 9, 2014

Related U.S. Application Data

(62) Division of application No. 12/738,618, filed as application No. PCT/AU2008/001551 on Oct. 21, 2008, now abandoned.

(30) Foreign Application Priority Data

Oct. 22, 2007  (AU) .................................. 2007905753
Mar. 19, 2008  (AU) .................................. 2008901357

(51) Int. Cl.
| | | |
|---|---|---|
| *A61K 39/35* | (2006.01) | |
| *C07K 14/415* | (2006.01) | |
| *C07K 16/16* | (2006.01) | |
| *G01N 33/577* | (2006.01) | |

(52) U.S. Cl.
CPC ............ *A61K 39/35* (2013.01); *C07K 14/415* (2013.01); *C07K 16/16* (2013.01); *G01N 33/577* (2013.01)

(58) Field of Classification Search
None
See application file for complete search history.

(56) References Cited

U.S. PATENT DOCUMENTS

| | | | | |
|---|---|---|---|---|
| 6,008,340 A | * | 12/1999 | Ball ..................... | C07K 14/415 435/252.3 |
| 2004/0034888 A1 | * | 2/2004 | Liu ..................... | C07K 14/415 800/289 |
| 2004/0172684 A1 | * | 9/2004 | Kovalic ................ | C07H 21/04 800/284 |

FOREIGN PATENT DOCUMENTS

WO    WO 03/024998    *    3/2003    ............... C07K 7/08

OTHER PUBLICATIONS

Blumenthal et al. 'Definition of an allergen.' Allergens and Allergen Immunotherapy. Ed. R. Lockey, S. Bukantzand j. Bousquet. New York: Marcel Decker, 2004. pp. 37-50.*
Schein et al. 'Bioinformatics Approaches to Classifying Allergens and Predicting Cross-Reactivity.' Immunol. Allergy. Clin. North Am. 27(1):1-27, 2007.*
Friedl-Hajek et al. Clin. Exp. Allerg. 29:478-487, 1999.*

* cited by examiner

*Primary Examiner* — Nora Rooney
(74) *Attorney, Agent, or Firm* — Knobbe Martens Olson & Bear LLP

(57) ABSTRACT

The present invention relates generally to novel recombinant polypeptides of Bahia grass pollen and to genetic sequences encoding same. More particularly, the present invention is directed to Pas n 1 polypeptides and derivatives, and fragments thereof and genetic sequences encoding same. The molecules of the present invention are useful in a range of therapeutic, prophylactic and diagnostic applications including, but not limited to, applications in the context of conditions characterized by an aberrant, inappropriate or otherwise unwanted immune response to the Bahia grass pollen.

7 Claims, 6 Drawing Sheets

FIGURE 6

```
                1         11         21         31         41         51
consensus      ------M SSS --VLLVVAL AVF G A GIPKVPPGPNITATYGDKWLDAKSTWYG-K
Lol_p_1        .......A...S.........F...L.S.H..A..........E................
Pha_a_1        MMKMVCSS...S..L.V.A..L...V.S.Q..A..........E................
Hol_l_1        ....MASS.R.V..L...A..F...L.S.H..A..........E................
Dac_g_1        .....MAS...S.........F...L.S.H...............................
Phl_p_1        .......A...S........V.F..L.S.Y...............................
Poa_p_1        .......A...S.........F...L.T.H..A............................
Sor_h_1        .......SW.MQ...A.....AFLVG.AWC.P...A..K.......SD..ER.A.......
Ory_s_1        .......A...L..L.AC.VVA.MVSAVSC.P..........TS......E..A.....A
Cyn_d_1        ......----ML..AAVA.V.ASMVG.AWCAMGDK-..................A.F..SD
Zea_m_1        .......G.LANNIMVVGAV.A.LVV.GSC.P..........TN.NG...T.RA.....Q
Pas_n_1        .......G.LAK.I.AVAAV.A.LVA.GSC.P..........TN.NG...P..A.....Q 61        71        81        91        101       111
consensus      PTGAGPKDNGGACGYKDVDKAPF GMTGCGNTPIFKDGRGCGSCFEIKC KPE CSGEPV
Lol_p_1        ................N......N......................T...S....A.
Pha_a_1        ................N.............................L..S...S.....I
Hol_l_1        ...............P..S............................T...S......
Dac_g_1        ................N..............................T...S....A.
Phl_p_1        ...............P..S.............S..............T...A......
Poa_p_1        .................S..............S..............T...S......
Sor_h_1        .....D..........N..NS.GA....L..........D..AE....A.
Ory_s_1        .K...........L..NS...D......K............S...A..DK.A
Cyn_d_1        .R..A.D.H..........D......E......L.....Y....KE.AE.....
Zea_m_1        .N....AP.......I.N.NLP.YS...A....V......K.....Y.VR.KEKPE...N..
Pas_n_1        .N....D........I.N.NLP.YN.F.A....P......K.....Y..R.N-KPE...Q...

121       131       141       151       161       171
consensus      TVHITDDNEEPIAPYHFDLSG AFGAMAKKGEE KLR AGELELQFRRVKCKYP GTK T
Lol_p_1        ..T..................H...S.......QNV.S...............DD..P.
Pha_a_1        ....................H...S.......ENV.G.................D...P.
Hol_l_1        ....................H...S.......Q...S........K........D...P.
Dac_g_1        ....................H...S.......Q...S.................E...V.
Phl_p_1        V...................H....D.Q...S.......................E...V.
Poa_p_1        L.........A.......K.............Q...S......K........E..E...V.
Sor_h_1        V.....M.Y.Q..A......A.T...........E...K..IIDMK.........---.E.V.
Ory_s_1        LI.V..M.D....A.......L.......D.KDEE..K..IIDT..........AD..I.
Cyn_d_1        LIK...K.Y.H..A........K........D...K....M......E..SD..I.
Zea_m_1        ..F...M.Y...........K...SL..P.LND...HC.IMDVE....R....A.Q.IV
Pas_n_1        ..F...M.Y...........K.......P.LND...HY.IFD.E....R...QG.Q.IV 181       191       201       211       221       231
consensus      FHVEKGSNPNYLALLVKYV GDGDVVAVDIKEKGKDKWI LKESWGAIWR DTPDKLTGP
Lol_p_1        .....A.......I.....D....................E........V..I.........
Pha_a_1        .................D......................E.............I.........
Hol_l_1        ................ID......................E............V..V.........
Dac_g_1        .................D......................A.............V.........
Phl_p_1        .................N......................E.............I.........
Poa_p_1        .................T......................E........S...V.........
Sor_h_1        .................D......G......G.AYQP..H........K.SDKPIKF.
Ory_s_1        ..I..A...........A......E.E.....SEE.KA..........I...KP.K..
Cyn_d_1        .......S........AA...NI.G....P..S.VFLPM.L......M.P.KP.K..
Zea_m_1        ..I...C....V.V...F.AD...I.LME.QD.LSAE.KPM.L.......M..AKA.K..
Pas_n_1        .............M...F.AD...I.LMEL...-SSD.KPM.L.......M...KA.VP.

241       251       261       271
consensus      PTVRYTTEGGTK EAEDVIPEGWKADT Y SK----
Lol_p_1        ............S.F............S.SA.....
Pha_a_1        ............A.F............HDA......
Hol_l_1        ............G..............A.EA.....
Dac_g_1        ............S.V............S.EA.....
Phl_p_1        ............T..............S.E......
Poa_p_1        ............G..............A.A......
Sor_h_1        V..QI.......TAY............T.TA.....
Ory_s_1        .S..V.....E.II...A..D.....SV.K.NVQAK
Cyn_d_1        ..I.L.S.S.GHV.Q......D..P..V.K..IQF.
Zea_m_1        .SI.L.S.S.K.VI.K.I..AN.RP.AV.T.NVQFY
Pas_n_1        .SI.L.S.S.K.VI.Q....VN..P..V.N.NVQF.
```

IMMUNOGENIC PROTEIN PAS N 1 FROM BAHIA GRASS POLLEN

CROSS REFERENCE TO RELATED APPLICATIONS

This application is a divisional of and claims the benefit and priority to U.S. patent application Ser. No. 12/738,618, filed on Sep. 28, 2010, which is a U.S. National Phase application of PCT International Application Number PCT/AU2008/001551, filed on Oct. 21, 2008, designating the United States of America and published in the English language, which is an International Application of and claims the benefit of priority to United Australian Patent Application No. 2007905753, filed on Oct. 22, 2007, and Australian Patent Application No. 2008901357, filed on Mar. 19, 2008. The disclosures of the above-referenced applications are hereby expressly incorporated by reference in their entireties.

REFERENCE TO SEQUENCE LISTING

The present application is being filed along with a sequence listing in electronic format. The sequence listing is provided as a file entitled SeqList-FISHR37-001D1.txt, created Jun. 20, 2014 which is 11 KB in size, and updated by a file entitled SeqList-FISHR37-001D1Replacement.txt, created on Aug. 16, 2016, which is 36 KB in size. The information in the electronic format of the sequence listing is incorporated herein by reference in its entirety.

FIELD OF THE INVENTION

The present invention relates generally to novel recombinant polypeptides of Bahia grass pollen and to genetic sequences encoding same. More particularly, the present invention is directed to Pas n 1 polypeptides and derivatives, and fragments thereof and genetic sequences encoding same. The molecules of the present invention are useful in a range of therapeutic, prophylactic and diagnostic applications including, but not limited to, applications in the context of conditions characterised by an aberrant, inappropriate or otherwise unwanted immune response to the Bahia grass pollen.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge in Australia.

The frequency of atopy and the incidence of allergic diseases, such as seasonal rhinitis, have increased in recent decades, hereby making the characterisation of causative allergens a priority (Robinson et al. Linnenborg et al., 2001). Grass pollen, in particular, are linked to the onset of allergy in a very significant proportion of the population.

Bahia grass, *Paspalum notatum*, is endemic to sub-tropical parts of the Americas near the equator and has been introduced elsewhere, including Australia, as lawn, feed crop or under-planting ground cover in orchards (Firth). Bahia grass is a perennial warm weather bunch grass with a deep root system that grows well on all soils in wet areas. Production of pollen is moderate to heavy. Bahia grass pollen is capable of provoking an immediate hypersensitivity type I reaction in patients who are allergic to either this grass source or to pollen of Bermuda grass or other members of the subfamily Pooideae. Previous studies also indicate that patients allergic to the pollen of some trees also show strong reactivity to Bahia grass. Whilst the major temperate grass species including Timothy and Ryegrass pollinate during spring and early summer, triggering seasonal allergic rhinitis and asthma in sensitized individuals, the pollination period of Bahia grass extends from spring through to autumn, thereby often triggering allergic symptoms late in the grass pollen season. Accordingly, Bahia grass is recognised as an important allergen source for triggering allergic rhinitis and seasonal asthma (Davies et al., 2005; Weber et al. 2006).

To this end, the Group I allergens of grass pollen are important because they are clinically significant allergens which play a vital biological role in fertilization of the grass. They are major allergens which react at a frequency greater than 90% with serum IgE of allergic individuals. The Group I allergens generally comprise up to 4% of the total pollen protein, making them a major component of the pollen (Yennawar et al., 2006). However, they are critical not only because of their abundance but because of their function.

In terms of Bahia-related allergy, it has been reported that immunotherapy with a mixture of Timothy and Bermuda grass pollen extract could diminish wheals induced by allergen skin prick testing in response to 10 grasses including Bahia grass. It would suggest that inclusion of Bahia grass pollen may not be required for an effective grass pollen immunotherapy extract for seasonal allergy (Phillips et al., 1989). However, whereas Bahia grass is allergenic in nasal challenges, it is not cross reactive with Timothy grass pollen by nasal challenge, indicating that immunotherapy vaccines lacking Bahia grass may not effectively treat Bahia grass pollen allergy (Phillips et al., 1989).

Only limited IgE cross-reactivity between ryegrass and Bahia grass has been found, consistent with the distinct phylogeny of these grasses (Davies et al., 2005). Bahia grass is phylogenetically distinct from ryegrass and Timothy grass. While these two and other well characterised allergenic grass species belong to the Pooideae subfamily of temperate grasses, Bahia grass resides in the Pancoideae sub-family. Accordingly, despite the importance of Bahia protein as an allergen, the allergens of Bahia grass have not been characterised or defined. The availability of cloned individual allergens of Bahia grass pollen would facilitate investigation of IgE and T cell cross-reactivity, as well as providing reagents for component based immunology vaccines candidates for desensitisation of Bahia grass pollen allergy, In work leading up to the present invention, the major Group I grass pollen allergen of Bahia grass has been identified, characterised and cloned. The identification of this allergen now facilitates the development of molecules and methods for the diagnosis and treatment of conditions such as those characterised by an aberrant, inappropriate or otherwise unwanted immune response to Bahia pollen.

SUMMARY OF THE INVENTION

Throughout this specification and the claims that follow, unless the context requires otherwise, the word "comprise", or variations such as "comprises" or "comprising" will be understood to imply the inclusion of a stated element or integer or group of elements or integers, but not the exclusion of any other element or integer or group of elements or integers.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The subject specification contains amino acid and nucleotide sequence information prepared using the programme PatentIn Version 3.1, presented herein after the bibliography. Each amino acid and nucleotide sequence is identified in the sequence listing by the numeric indicator <210> followed by the sequence identifier (eg. <210>1, <210>2, etc). The length, type of sequence (amino acid, DNA, etc.) and source organism for each sequence is indicated by information provided in the numeric indicator fields <211>m<212> and <213>, respectively. Amino acid and nucleotide sequences referred to in the specification are identified by the indicator SEQ ID NO: followed by the sequence identifier (eg. SEQ ID NO:1, SEQ ID NO: 2, etc). The sequence identifier referred to in the specification correlates to the information provided in numeric indicator field <400> in the sequence listing, which is followed by the sequence identifier (eg. <400>1, <400>2, etc). That is SEQ ID NO: 1 as detailed in the specification correlates to the sequence indicated as <400>1 in the sequence listing.

One aspect of the present invention is directed to a nucleic acid molecule which encodes, or is complementary to a nucleic acid molecule which encodes, a Group I grass pollen allergen from Bahia grass or derivative or fragment thereof, wherein said allergen is Pas n 1.

Another aspect of the present invention is directed to an isolated nucleic acid mole selected from the list consisting of:

(i) An isolated nucleic acid molecule or fragment, derivative or mutant thereof comprising a nucleotide sequence encoding, or complementary to a sequence encoding, an amino acid sequence substantially as set forth in SEQ ID NO:2 or 4 or a fragment or derivative thereof, or an amino acid sequence having at least 86%, 87%, 88%, 89%, 90%, 91%, 92%, 93%, 94%, 95%, 96%, 97%, 98% or 99% or more sequence identity to SEQ ID NO:2 or 4 over the length of the sequence or a nucleic acid sequence capable of hybridizing to said nucleic acid molecule under low stringency conditions;

(ii) An isolated nucleic acid molecule or fragment or derivative thereof comprising a nucleotide sequence, or complementary to said sequence, wherein said nucleotide sequence is substantially as set forth in SEQ ID NO:1 or 3 or a nucleotide sequence having at least about 86%, 87%, 88%, 89%, 90%, 91%, 92%, 93%, 94%, 95%, 96%, 97%, 98% or 99% or more identity over the length of the sequence or a nucleotide sequence capable of hybridising to SEQ ID NO:1 or 3 or complementary form thereof under low stringency conditions; or (iii) An isolated nucleic acid molecule or derivative or fragment thereof comprising a nucleotide sequence substantially as set forth in SEQ ID NO:1 or 3 or a functional fragment of said molecule.

Yet another aspect of the present invention is directed to a Group I grass pollen allergen protein from Bahia grass or a fragment or derivative thereof, wherein said protein is Pas n 1.

In still another aspect, said Pas n 1 comprises the sequence set forth in SEQ ID NO:2 or 4 or is a fragment or derivative thereof.

Yet still another aspect of the present invention is directed to an isolated protein as set forth in SEQ ID NO:2 or 4 or having at least about 86% or greater identity to SEQ ID NO:2 or 4 across the length of the sequence or a fragment or derivative thereof.

Still another aspect of the present invention is directed to a protein or derivative or fragment thereof encoded by the nucleotide sequence as set forth in SEQ ID NOs:1 or 3 or the sequence complementary to a sequence capable of hybridising to SEQ ID NOs:1 or 3 under low stringency conditions and which encodes an amino acid sequence as set forth in SEQ ID NOs:2 or 4 or having at least about 86% or greater identity to SEQ ID NOs:2 or 4 across the length of the sequence.

A further aspect of the invention provides a method of producing recombinant Pas n 1 in a cell, said method comprising expressing in said cell a nucleic acid molecule which encodes or is complementary to a nucleic acid molecule which encodes said Pas n 1.

Another further aspect of the invention provides an isolated cell which expresses an endogenous or recombinant Pas n 1 protein or a functional fragment or derivative thereof.

In a related aspect, the present invention provides a method of producing a recombinant Pas n 1 in a cell comprising the steps of:

(i) introducing into said cell a genetic construct comprising a nucleic acid molecule which encodes or is complementary to a nucleic acid molecule which encodes said Pas n 1; and (ii) culturing said cell for a time and under conditions sufficient for said nucleic acid molecule to be expressed.

Yet another aspect of the present invention provides a method for identifying a Pas n 1 nucleic acid molecule or a fragment or derivative thereof.

In still another aspect the present invention provides a method for the treatment and/or prophylaxis of a subject, said method comprising administering to said subject an effective amount of a Pas n 1 protein or nucleic acid molecule or an antibody directed to Pas n 1 as hereinbefore defined.

Yet still another aspect of the present invention contemplates the use of a Pas n 1 protein or nucleic acid molecule or an antibody directed to Pas n 1 as hereinbefore defined in the manufacture of a medicament for the treatment of a condition in a mammal.

Still yet another aspect of the present invention is directed to the use of a Pas n 1 protein or nucleic acid molecule or an antibody directed to Pas n 1 as hereinbefore defined for therapy or prophylaxis.

In yet another further aspect, the present invention contemplates a pharmaceutical composition comprising a molecule as hereinbefore defined and one or more pharmaceutically acceptable carriers and/or diluents.

Another aspect of the present invention is directed to a method of diagnosing or monitoring a condition in a mammal, which condition is characterised by an aberrant, unwanted or inappropriate response to Pas n 1, said method comprising screening for Pas n 1 T or B cell reactivity.

Still another aspect of the present invention is directed to detecting the presence of Pas n 1 or a fragment or derivative thereof in a sample.

In another aspect, the present invention provides diagnostic kits for use in the methodology hereinbefore defined.

Single and three letter abbreviations used throughout the specification are defined in Table 1.

TABLE 1

Single and three letter amino acid abbreviations

| Amino Acid | Three-letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | The | T |
| Tryptophan | Trp | W |
| Tyrosine | Tyr | Y |
| Valine | Val | V |
| Any residue | Xaa | X |

BRIEF DESCRIPTION OF THE DRAWINGS

FIG. 6 is a multiple sequence alignment of known Group I grass pollen allergens. Clustal W alignment of the isoform closest to Pas n 1 from each grass species identified by BLAST search of the SwissProt and SpTrEMBL databases. Sor h 1 sequence of Johnson grass obtained from Avjioglu (U.S. Pat. No. 5,736,149, Apr. 7, 1998). Sequence designations are as follows: Consensus: SEQ ID NO:23; Lol p 1: SEQ ID NO:24; Pha a 1: SEQ ID NO:25; Hol l 1: SEQ ID NO:26; Dac g 1: SEQ ID NO:27; Phi p 1: SEQ ID NO:28; Poa p 1: SEQ ID NO:29; Sor h 1: SEQ ID NO:30; Ory s 1: SEQ ID NO:31: Cyn d 1: SEQ ID NO:32 Zea m 1: SEQ ID NO:33; Pas n 1: SEQ ID NO:2.

DETAILED DESCRIPTION OF THE INVENTION

Figure 1:
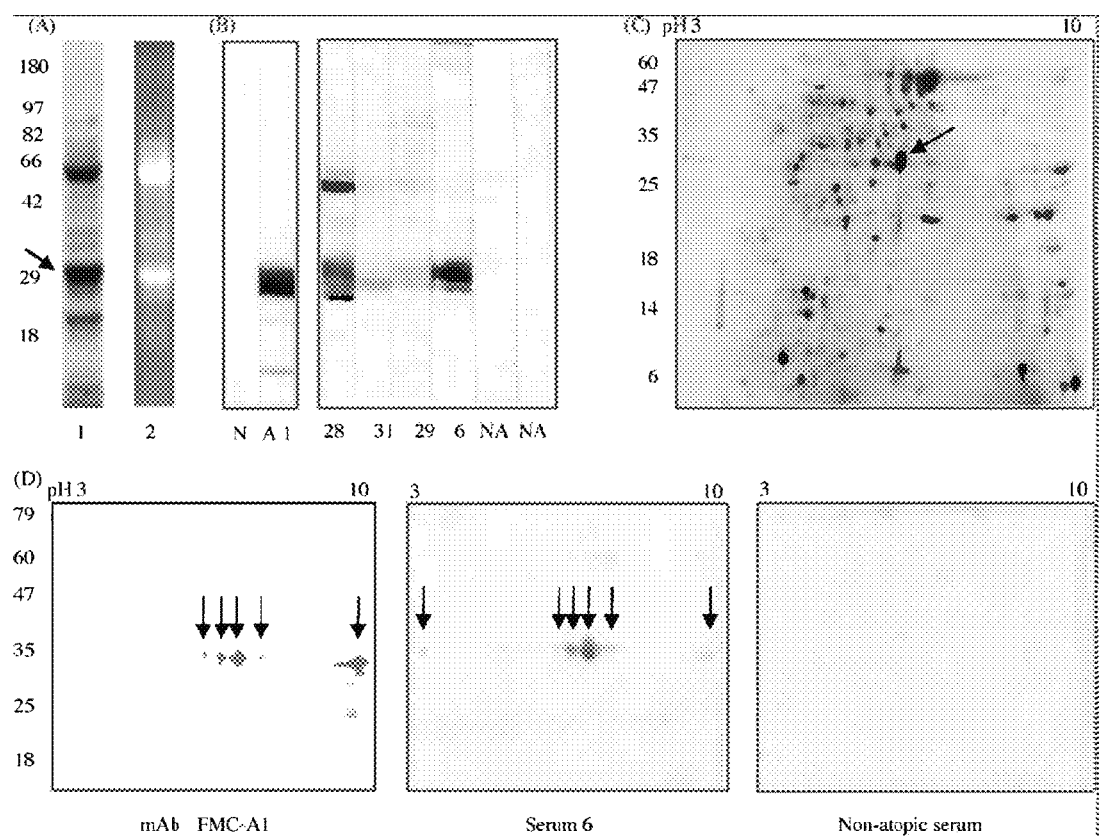
FIG. 1 is an image of the identification of the group allergens of Bahia grass pollen (BaGP) extract. (A) SDS-PAGE of BaGP extract stained with CBB (left panel) and for glycoprotein (right panel). The arrow indicates group 1 allergen band. (B) Immunoblots probed with (A1) or without (N) mAb FMC-A1 (left panel) or for IgE reactivity with sera from BaGP-allergic subjects (Table 5) and atopic non-grass pollen-allergic subjects (NA). (C) Two-dimensional SDS-PAGE analysis of BaGP extract stained with CBB. The arrow marks the predominant group 1 allergen spot sent for N-terminal peptide sequencing. (D) Immunoblots of BaGP extract separated by two-dimensional SDS-PAGE shoeing reactivity with mAb FMC-A1 (left), BaGP-allergic patient 6 serum IgE (middle) and non-atopic serum IgE (right). Isoforms of the group 1 allergen are indicated by arrows.

The present invention is predicted, in part, on the cloning, expression and characterisation of the major Group I pollen allergen, Pas n 1, of Bahia grass. This finding provides novel protein and nucleic acid molecules for use, inter alia, in immune modulation. Accordingly, the identification of this novel Bahia grass pollen allergen has enabled the development of a new range of diagnostic, therapeutic and prophylactic reagents and treatment regimes for conditions such as, but not limited to, Bahia grass pollen allergy.

Accordingly, one aspect of the present invention is directed to a nucleic acid molecule which encodes, or is complementary to a nucleic acid molecule which encodes, a Group I grass pollen allergen from Bahia grass or derivative or fragment thereof, wherein said allergen is Pas n 1.

Reference to "Pas n 1" should be understood as including reference to all forms of Pas n 1, or derivatives or fragments thereof. Without limiting the present invention to any one theory or mode of action natural grass pollen allergens are well known to exhibit a wide variety of isoforms which may be expressed at different stages of maturation. Accordingly reference to "Pas n 1" should be understood to encompass all protein isoforms of Pas n 1 or derivatives or fragments which may arise from alternative splicing of Pas n 1 mRNA. Reference to "Pas n 1" also includes reference to polymorphic variants of Pas n 1. The present invention thereby provides nucleic acids and proteins for use in the diagnosis and treatment of any suitable condition, such as those characterised by hypersensitivity to a Pas n 1 or a Pas n 1-like molecule, for example Bahia grass pollen allergies or asthma. Preferably, said Pas n 1 polypeptide comprises the sequence set forth in SEQ ID NO: 2 or 4 or is a fragment or derivative of said sequence.

Accordingly, another aspect of the present invention is directed to an isolated nucleic acid mole selected from the list consisting of:

(i) An isolated nucleic acid molecule or fragment or derivative thereof comprising a nucleotide sequence encoding, or complementary to a sequence encoding, an amino acid sequence substantially as set forth in SEQ ID NO:2 or 4 or a fragment or derivative thereof, or an amino acid sequence having at least 86%, 87%, 88%, 89%, 90%, 91%, 92%, 93%, 94%, 95%, 96%, 97%, 98% or 99% or more sequence identity to SEQ ID NO:2 or 4 over the length of the sequence or a nucleic acid sequence capable of hybridizing to said nucleic acid molecule under low stringency conditions;

(ii) An isolated nucleic acid molecule or fragment or derivative thereof comprising a nucleotide sequence, or complementary to said sequence, wherein said nucleotide sequence is substantially as set forth in SEQ ID NO:1 or 3 or a nucleotide sequence having at least about 86%, 87%, 88%, 89%, 90%, 91%, 92%, 93%, 94%, 95%, 96%, 97%, 98% or 99% or more identity over the length of the sequence or a nucleotide sequence capable of hybridising to SEQ ID NO:1 or 3 or complementary form thereof under low stringency conditions; or (iii) An isolated nucleic acid molecule or derivative or fragment thereof comprising a nucleotide sequence substantially as set forth in SEQ ID NO:1 or 3 or a functional fragment of said molecule.

The present invention should be understood to extend to the genomic DNA form of the cDNA nucleotide sequences detailed above. To this end, SEQ ID NO:1 corresponds to Pas n 1 cDNA, including the sequence encoding the signal peptide. SEQ ID NO:3 corresponds to the sequence encoding the Pas n 1 cDNA open reading frame of the mature protein, i.e. the protein without the signal sequence. SEQ ID NO:2 corresponds to the Pas n 1 protein which includes the signal sequence while SEQ ID NO:4 corresponds to the Pas n 1 protein which does not include the signal sequence.

Reference herein to the genomic and cDNA forms of Pas n 1 is to be understood in its broadest context and includes:

(i) a classical genomic gene consisting of transcriptional and/or translational regulatory sequences and/or a coding region and/or non-translated sequences (i.e. introns, 5'- and 3'-untranslated sequences);

(ii) mRNA or cDNA corresponding to the coding regions (i.e. exons) optionally comprising 5'- or 3'-untranslated sequences of the gene; and/or (iii) mRNA or cDNA corresponding to the coding region either with or without sequences associated with precursor forms of the protein, such as signal sequences, and optionally 5'- or 3'-untranslated sequences.

As hereinbefore described, Pas n 1 corresponds to a previously unidentified Group I pollen allergen of Bahia grass.

Without limiting the present invention to any one theory or mode of action, the Group I grass pollen allergens are considered part of a superfamily of plant cell wall proteins called expansins. Accordingly, Pas n 1 as described herein corresponds to a 265 amino acid β-expansin glycoprotein including a 23 residue signal peptide sequence, with a pI of 9.73. It should therefore be understood that the present invention also extends to the expression product of the nucleic acid molecule as hereinbefore defined.

Accordingly, another aspect of the present invention is directed to a Group I grass pollen allergen protein from Bahia grass or a fragment or derivative thereof, wherein said protein is Pas n 1.

Preferably, said Pas n 1 comprises the sequence set forth in SEQ ID NO:2 or 4 or is a fragment or derivative thereof.

Yet another aspect of the present invention is directed to an isolated protein as set forth in SEQ ID NO:2 or 4 or having at least about 86% or greater identity to SEQ ID NO:2 or 4 across the length of the sequence or a fragment or derivative thereof.

The term "protein" should be understood to encompass peptides, polypeptides and proteins. It should also be understood that these terms are used interchangeably herein. The protein may be glycosylated or unglycosylated and/or may contain a range of other molecules fused, linked, bound or otherwise associated with the protein such as amino acids, lipids, carbohydrates or other peptides, polypeptides or proteins. Reference hereinafter to a "protein" includes a protein comprising a sequence of amino acids as well as a protein associated with other molecules such as amino acids, lipids, carbohydrates or other peptides, polypeptides or proteins.

Preferably, said 86% or greater similarity is a reference to 86%, 87%, 88%, 89%, 90%, 91%, 92%, 93%, 94%, 95%, 96%, 97%, 98% or 99% similarity.

The protein of the present invention is preferably in isolated form. By "isolated" is meant a protein having undergone at least one purification step and this is conveniently defined, for example, by a composition comprising at least about 10% subject protein, preferably at least about 20%, more preferably at least about 30%, still more preferably at least about 40-50%, even still more preferably at least about 60-70%, yet even still more preferably 80-90% or greater of subject protein relative to other components as determined by molecular weight, amino acid sequence or other convenient means. The protein of the present invention may also be considered, in a preferred embodiment, to be biologically pure.

As used herein, in terms of both the claimed proteins and nucleic acid molecules, the term "isolated" means that the material is removed from its original environment (e.g., the natural environment if it is naturally occurring). For example, a naturally occurring polynucleotide or protein present in a living plant is not isolated, but the same polynucleotide or protein, separated from some or all of the coexisting materials in the natural system, is isolated. Such polynucleotides could be part of a vector and/or such polynucleotides or protein could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

Proteins of the invention can be isolated from natural sources, be synthetic, or be recombinantly generated polypeptides. Peptides and proteins can be recombinantly expressed in vitro or in vivo. The proteins of the invention can be made and isolated using any method known in the art. Proteins of the invention can also be synthesized, whole or in part, using chemical methods well known in the art. See e.g., Caruthers et al. (1980) *Nucleic Acids Res. Symp. Ser.* 215-223; Horn et al. (1980) *Nucleic Acids Res. Symp. Ser.* 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge et al. (1995) *Science* 269:202; Merrifield (1997) *Methods Enzymol.* 289:3-13) and automated synthesis may be achieved, e.g., using the ABI 431A Peptide Synthesizer (Perkin Elmer) in accordance with the instructions provided by the manufacturer.

Proteins of the invention can also be synthesised and expressed as fusion proteins with one or more additional domains linked thereto for example, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising protein to facilitate purification. For example, an expression vector can include an epitope-encoding nucleic acid sequence linked to six histidine residues followed by a thioredoxin and an enterokinase cleavage site (see e.g., Williams et al. (1995) *Biochemistry* 34:1787-1797; Dobeli et al. (1998) *Protein Expr. Purif.* 12:404-14). The histidine residues facilitate detection and purification while the enterokinase cleavage site provides a means for purifying a region from the remainder of the fusion protein. Technology pertaining to vectors encoding fusion proteins and application of fusion proteins are well described in the scientific and patent literature, see e.g., Kroll et al. (1993) *DNA Cell. Biol.*, 12:441-53.

Notwithstanding that the present invention encompasses recombinant proteins, chemical synthetic techniques are also contemplated in the synthesis of the subject proteins.

A chemically systhesised protein according to the present invention is conveniently synthesised based on molecules isolated from Bahia grass pollen. Isolation of these molecules may be accomplished by any suitable means such as by chromotographic separation, for example using CM-cellulose ion exchange chromatography followed by Sephadex (e.g. G-50 column) filtration. Many other techniques are available including HPLC, PAGE amongst others.

The subject protein may be synthesised by solid phase synthesis using F-moc chemistry as described by Carpino et al. (1991). Polypeptides and fragments thereof may also be synthesised by alternative chemistries including, but not limited to, t-Boc chemistry as described in Stewart et al. (1985) or by classical methods of liquid phase peptide synthesis.

Still another aspect of the present invention is directed to a protein or derivative or fragment thereof encoded by the nucleotide sequence as set forth in SEQ ID NOs:1 or 3 or the sequence complementary to a sequence capable of hybridising to SEQ ID NOs:1 or 3 under low stringency conditions and which encodes an amino acid sequence as set forth in SEQ ID NOs:2 or 4 or having at least about 86% or greater identity to SEQ ID NOs:2 or 4 across the length of the sequence.

The phrases "nucleic acid" or "nucleic acid sequence" as used herein refer to an oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) *Toxicol. Appl. Pharmacol.* 144:189-197; Strauss-Soukup et al. (1997) *Biochemistry* 36:8692-8698; Samstag et al. (1996) *Antisense Nucleic Acid Drug Dev* 6:153-156.

To this end, it should be understood that the present invention extends to antisense nucleic acid molecules which are directed to the Pas n 1 nucleic acid molecules herein defined.

A further aspect of the invention provides a method of producing recombinant Pas n 1 in a cell, said method comprising expressing in said cell a nucleic acid molecule which encodes or is complementary to a nucleic acid molecule which encodes said Pas n 1.

The nucleic acid molecule of the present invention is preferably in isolated form or ligated to a vector, such as an expression vector. By "isolated" is meant a nucleic acid molecule having undergone at least one purification step and this is conveniently defined, for example, by a composition comprising at least about 10% subject nucleic acid molecule, preferably at least about 20%, more preferably at least about 30%, still more preferably at least about 40-50%, even still more preferably at least about 60-70%, yet even still more preferably 80-90% or greater of subject nucleic acid molecule relative to other components as determined by molecular weight, amino acid sequence or other convenient means. The nucleic acid molecule of the present invention may also be considered, in a preferred embodiment, to be biologically pure.

The nucleic acids of the invention can be made, isolated and/or manipulated by, e.g., cloning and expression of cDNA libraries, amplification of mRNA or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed or generated recombinantly. Recombinant proteins generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) *J. Am. Chem. Soc.* 105:661; Belousov et al. (1997) supra; Frenkel et al. (1995) supra; Blommers et al. (1994) supra; Narang et al. (1979) *Meth. Enzymol.* 68:90; Brown et al. (1979) *Meth. Enzymol.* 68:109; Beaucage (1981) *Tetra. Lett.* 22:1859; U.S. Pat. No. 4,458,066.

The invention provides oligonucleotides comprising sequences of the invention, e.g., subsequences of the exemplary sequences of the invention. Oligonucleotides can include, e.g., single stranded poly-deoxynucleotides or two complementary polydeoxynucleotide strands which may be chemically synthesized.

Techniques for the manipulation of nucleic acids, such as, e.g., subcloning, labelling probes (e.g., random-primer labelling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Nucleic acids, vectors, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabelling, scintillation counting, and affinity chromatography.

The nucleic acids of the invention can be operably linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The invention provides expression vectors and cloning vehicles comprising nucleic acids of the invention, e.g., sequences encoding the proteins of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available.

The nucleic acids of the invention can be cloned, if desired, into any of a variety of vectors using routine molecular biological methods. Methods for cloning in vitro amplified nucleic acids are described, e.g., U.S. Pat. No. 5,426,039. To facilitate cloning of amplified sequences, restriction enzyme sites can be "built into" a PCR primer pair.

The invention provides libraries of expression vectors encoding polypeptides and peptides of the invention. These nucleic acids may be introduced into a genome or into the cytoplasm or a nucleus of a cell and expressed by a variety of conventional techniques, well described in the scientific and patent literature. See, e.g., Roberts et al. (1987) *Nature* 328:731; Schneider (1995) *Protein Expr. Purif.* 6435:10; Sambrook, Tijssen or Ausubel. The vectors can be isolated from natural sources, obtained from such sources as ATCC or GenBank libraries, or prepared by synthetic or recombinant methods. For example, the nucleic acids of the invention can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required.

The nucleic acid molecule may be ligated to an expression vector capable of expression in a prokaryotic cell (eg. *E. coli*) or a eukaryotic cell (eg. yeast cells, fungal cells, insect cells, mammalian cells or plant cells). The nucleic acid molecule may be ligated or fused or otherwise associated with a nucleic acid molecule encoding another entity such as, for example, a signal peptide. It may also comprise additional nucleotide sequence information fused, linked or otherwise associated with it either at the 3' or 5' terminal portions or at both the 3' and 5' terminal portions. The nucleic acid molecule may also be part of a vector, such as an expression vector. The latter embodiment facilitates production of recombinant forms of the subject peptide which forms are encompassed by the present invention.

Such nucleic acids may be useful for recombinant production Pas n 1 protein by insertion into an appropriate vector and transfection into a suitable cell line. Such expression vectors and host cell lines also form an aspect of the invention.

In producing proteins by recombinant techniques, host cells transformed with a nucleic acid having a sequence encoding a protein according to the invention are cultured in a medium suitable for the particular cells concerned. Proteins can then be purified from cell culture medium, the host cells or both using techniques well known in the art such as ion exchange chromatography, gel filtration chromatography, ultrafiltration, electrophoresis or immunopurification with antibodies specific for the peptide.

Nucleic acids encoding Pas n 1 or Pas n 1 proteins may be expressed in bacterial cells such as *E. coli*, insect cells, yeast or mammalian cells such as Chinese hamster ovary cells (CHO). Suitable expression vectors, promoters, enhancers and other expression control elements are referred to in Sambruck et al (Cold Spring Harbour Laboratory Press, 1989). Other suitable expression vectors, promoters, enhancers and other expression elements are well known to those skilled in the art. Examples of suitable expression vectors in yeast include Yep Sec 1 (Balderi et al., 1987, *Embo. J.,* 6:229-234); pMFa (Kurjan and Herskowitz, Cell, 30:933-943, 1982); JRY88 (Schultz et al., *Gene,* 54:113-123, 1987) and pYES2 (Invitrogen Corporation, San Diego, Calif.). These vectors are freely available as are baculovirus and mammalian expression systems. For example, a baculovirus system is commercially available (ParMingen, San Diego, Calif.) for expression in insect cells while the pMsg vector is commercially available (Pharmacia, Piscataway, N.J.) for expression in mammalian cells.

For expression in *E. coli* suitable expression vectors include among others, pTrc (Amann et al, *Gene,* 69:301-315, 1988) pGex (Amrad Corporation, Melbourne, Australia); pMal (N.E. Biolabs, Beverley, Mass.); pRit5 (Pharmacia, Piscataway, N.J.); pEt-11d (Novagen, Maddison, Wis.) (Jameel et al., *J. Virol.,* 64:3963-3966 1990) and pSem (Knapp et al., *Bio Techniques,* 8:280-281, 1990). The use of pTRC, and pEt-11d, for example, will lead to the expression of unfused protein. The use of pMal, pRit5, pSem and pGex will lead to the expression of allergen fused to maltose E binding protein (pMal), protein A (pRit5), truncated-galactosidase (PSEM) or glutathione S-transferase (pGex). When Pas n 1 is expressed as a fusion protein, it is particularly advantageous to introduce an enzymatic cleavage site at the fusion junction between the carrier protein and the polypeptide concerned. The polypeptide of the invention may then be recovered from the fusion protein through enzymatic cleavage at the enzymatic site and biochemical purification using conventional techniques for purification of proteins and peptides. Examples of enzymatic cleavage sites include those for blood clotting factor Xa or thrombin for which the appropriate enzymes and protocols for cleavage are commercially available. The different vectors also have different promoter regions allowing constitutive or inducible expression or temperature induction. It may additionally be appropriate to express recombinant polypeptides in different *E. coli* hosts that have an altered capacity to degrade recombinantly expressed proteins. Alternatively, it may be advantageous to alter the nucleic acid sequence to use codons preferentially utilised by *E. coli*, where such nucleic acid alteration would not affect the amino acid sequence of the expressed proteins.

Host cells can be transformed to express the nucleic acids of the invention using conventional techniques such as calcium phosphate or calcium chloride co-precipitation, DEAE-dextran-mediated transfection or electroporation. Suitable methods for transforming the host cells may be found in (Sambruck et al., 1989), and other laboratory texts. The nucleic acid sequence of the invention may also be chemically synthesised using standard techniques.

The term "expression cassette" as used herein refers to a nucleotide sequence which is capable of effecting expression of a structural gene (i.e., a protein coding sequence, such as a polypeptide of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. "Operably linked" as used herein refers to linkage of a promoter upstream from a DNA sequence such that the promoter mediates transcription of the DNA sequence. Thus, expression cassettes also include plasmids, expression vectors, recombinant viruses, any form of recombinant "naked DNA" vector, and the like.

A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and includes both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

For optimum expression in a particular cell or under specified conditions, the nucleic acid molecule may be placed operably under the control of a promoter sequence such as those discussed earlier. Suitable cells and virus particles for this purpose are also discussed earlier. Promoter sequences and culture conditions for cells or virus particles which produce high levels of expression will be well-known to those skilled in the relevant art.

Accordingly, the present invention also provides a transformed cell comprising a nucleic acid sequence of the invention, e.g., a sequence encoding the protein of the invention, or a vector of the invention. The host cell may be any of the host cells familiar to those skilled in the art, including prokaryotic cells, such as bacterial cells, eukaryotic cells, such as fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Reference herein to "Pas n 1" should be understood as a reference to the nucleic acid and protein molecules hereinbefore described.

Engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired protein or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed protein or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Accordingly, a further aspect of the invention provides an isolated cell which expresses an endogenous or recombinant Pas n 1 protein or a functional fragment or derivative thereof.

Alternatively, the isolated cell may be a transformed eukaryotic cell which expresses a Pas n 1 protein via a genetic construct, such as those discussed earlier. Means for introducing genetic constructs into a cell have been defined herein and will be well-known to those skilled in the art.

Means for isolating a cell which expresses an endogenous or recombinant Pas n 1 protein have also been discussed herein and will be well-known to those skilled in the art.

The terms "similarity" and "identity" as used herein include exact identity between compared sequences at the nucleotide or amino acid level. Where there is non-identity at the nucleotide level, "similarity" and include "identity" differences between sequences which may encode different amino acids that are nevertheless related to each other at the structural, functional, biochemical and/or conformational levels. In a particularly preferred embodiment, nucleotide sequence comparisons are made at the level of identity rather than similarity.

Terms used to describe sequence relationships between two or more polynucleotides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (*Nucl. Acids Res.* 25: 3389, 1997). A detailed discussion of sequence analysis can be found in Unit 19.3 of Ausubel et al. ("Current Protocols in Molecular Biology" John Wiley & Sons Inc, Chapter 15, 1994-1998). A range of other algorithms may be used to compare the nucleotide and amino acid sequences such as but not limited to PILEUP, CLUSTALW, SEQUENCHER or VectorNTI.

The terms "sequence similarity" and "sequence identity" as used herein refers to the extent that sequences are identical or functionally or structurally similar on a nucleotide-by-nucleotide basis over a window of comparison. Thus, a "percentage of sequence identity", for example, is calculated by comparing two optimally aligned sequences over the window of comparison, determining the number of positions at which the identical nucleic acid base (e.g. A, T, C, G, I) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

As detailed above, and more specifically, protein and/or nucleic acid sequence identities (homologies) may be evaluated using any of the variety of sequence comparison algorithms and programs known in the art. The extent of sequence identity (homology) may be determined using any computer program and associated parameters, including those described herein, such as BLAST 2.2.2. or FASTA version 3.0t78, with the default parameters. For example, the sequence comparison algorithm is a BLAST version algorithm. In one aspect, for nucleic acid sequence identity analysis, the BLAST nucleotide parameters comprise word size=11, expect=10, filter low complexity with DUST, cost to open gap=5, cost to extend gap=2, penalty for mismatch=−3, reward for match=1, Dropoff (X) for BLAST extensions in bits=20, final X dropoff value for gapped alignment=50, and all other options are set to default. In one aspect, for polypeptide sequence identity analysis the sequence comparison algorithm is a BLAST version algorithm, e.g., where the BLAST nucleotide parameters comprise word size=3, expect=10, filter low complexity with SEG, cost to open gap=11, cost to extend gap=1, similarity matrix Blosum62, Dropoff (X) for blast extensions in bits=7, X dropoff value for gapped alignment (in bits)=15, final X dropoff value for gapped alignment=25.

Exemplary algorithms and programs include, but are not limited to, TBLASTN, BLASTP, FASTA, TFASTA, and CLUSTALW (Pearson and Lipman, *Proc. Natl. Acad. Sci. USA* 85(8):2444-2448, 1988; Altschul et al., *J. Mol. Biol.* 215(3):403-410, 1990; Thompson et al., *Nucleic Acids Res.* 22(2):4673-4680, 1994; Higgins et al., *Methods Enzymol.* 266:383-402, 1996; Altschul et al., *Nature Genetics* 3:266-272, 1993). Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications.

BLAST, BLAST 2.0 and BLAST 2.2.2 algorithms are also used to practice the invention. They are described, e.g., in; Altschul et al. (1990), supra. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul et al. (1990) supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) $Proc.\ Natl.\ Acad.\ Sci.\ USA$ 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) $Proc.\ Natl.\ Acad.\ Sci.\ USA$ 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., $Science$ 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used, default options to blast. There are about 38 setting options in the BLAST 2.2.2 program. In this exemplary aspect of the invention, all default values are used except for the default filtering setting (i.e., all parameters set to default except filtering which is set to OFF); in its place a "−F F" setting is used, which disables filtering. Use of default filtering often results in Karlin-Altschul violations due to short length of sequence.

The default values used in this exemplary aspect of the invention include:
"Filter for low complexity: ON
Word Size: 3
Matrix: Blosum62
Gap Costs Existence:11
Extension:1"

Other default settings are: filter for low complexity OFF, word size of 3 for protein, BLOSUM62 matrix, gap existence penalty of −11 and a gap extension penalty of −1.

The terms "homology" and "identity" in the context of two or more nucleic acids or protein sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects of the invention, contiguous residues ranging anywhere from 20 to the full length of an exemplary polypeptide or nucleic acid sequence of the invention are compared to a reference sequence of the same number of contiguous positions after the two sequences are optimally aligned. If the reference sequence has the requisite sequence identity to an exemplary polypeptide or nucleic acid sequence of the invention, that sequence is within the scope of the invention.

The phrase "substantially identical" in the context of two nucleic acids or polypeptides, can refer to two or more sequences that have, e.g., at least about 86%, 87%, 88%, 89%, 90%, 91%, 92%, 93%, 94%, 95%, 96%, 97%, 98%, 99% or more sequence identity or more nucleotide or amino acid residue (sequence) identity, when compared and aligned for maximum correspondence, as measured using one any known sequence comparison algorithm, as discussed in detail below, or by visual inspection. In alternative aspects, the invention provides nucleic acid and polypeptide sequences having substantial identity to an exemplary sequence of the invention. Nucleic acid sequences of the invention can be substantially identical over the entire length of a polypeptide coding region.

To determine and identify sequence identities, structural homologies, motifs and the like in silico, the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

As used herein, the terms "computer," "computer program" and "processor" are used in their broadest general contexts and incorporate all such devices.

The invention provides isolated or recombinant nucleic acids that hybridize under low stringency conditions to an exemplary sequence of the invention. In alternative aspects, the stringent conditions are highly stringent conditions or medium stringent conditions, as known in the art and as described herein. These methods may be used to isolate nucleic acids of the invention.

In alternative aspects, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800 or more residues in length, or, the full length of a gene or coding sequence, e.g., cDNA. Nucleic acids shorter than full length are also included. These nucleic acids can be useful as, e.g., hybridization probes, labelling probes, PCR oligonucleotide probes, iRNA, antisense or sequences encoding antibody binding peptides (epitopes), motifs, active sites and the like.

"Hybridization" refers to the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m = 69.3 + 0.41$ (G+C) % (Marmur and Doty, *J. Mol. Biol.* 5: 109, 1962). However, the $T_m$ of a duplex DNA decreases by 1° C. with every increase of 1% in the number of mismatch base pairs (Bonner and Laskey, *Eur. J. Biochem.* 46: 83, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

Where nucleic acids of the invention are defined by their ability to hybridize under high stringency, these conditions comprise about 50% formamide at about 37° C. to 42° C. In one aspect, nucleic acids of the invention are defined by their ability to hybridize under reduced stringency comprising conditions in about 35% to 25% formamide at about 30° C. to 35° C. Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 n/ml sheared and denatured salmon sperm DNA). In one aspect, nucleic acids of the invention are defined by their ability to hybridize under reduced stringency conditions comprising 35% formamide at a reduced temperature of 35° C.

Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

The temperature range corresponding to a particular level of stringency can be further narrowed by calculating the purine to pyrimidine ratio of the nucleic acid of interest and adjusting the temperature accordingly. Nucleic acids of the invention are also defined by their ability to hybridize under high, medium, and low stringency conditions as set forth in Ausubel and Sambrook. Variations on the above ranges and conditions are well known in the art.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5°C from 68°C to 42°C in a hybridization buffer having a Na+ concentration of approximately 1M. Following hybridization, the filter may be washed with 2×SSC, 0.5% SDS at the temperature of hybridization. These conditions are considered to be "moderate" conditions above 50°C and "low" conditions below 50°C. A specific example of "moderate" hybridization conditions is when the above hybridization is conducted at 55°C. A specific example of "low stringency" hybridization conditions is when the above hybridization is conducted at 45°C.

Alternatively, the hybridization may be carried out in buffers, such as 6×SSC, containing formamide at a temperature of 42°C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50°C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

In a related embodiment, the present invention provides a method of producing a recombinant Pas n 1 in a cell comprising the steps of:

(i) introducing into said cell a genetic construct comprising a nucleic acid molecule which encodes or is complementary to a nucleic acid molecule which encodes said Pas n 1; and (ii) culturing said cell for a time and under conditions sufficient for said nucleic acid molecule to be expressed.

The term "derivative" as used herein includes portions, fragments and parts of the nucleic acid molecule or a translation product thereof. A derivative may also comprise a single or multiple nucleotide or amino acid substitution, deletion and/or addition but which substitution, deletion and/or addition does not alter the functional activity of said Pas n 1 protein. To this end, reference to a "functional" protein or nucleic acid should be understood as a reference to a protein or nucleic acid which exhibits the same functional activity as the molecule of which it is a derivative. A derivative of the nucleic acid molecule of the present invention also includes nucleic acid molecules capable of hybridising to the nucleotide sequence set forth in SEQ ID NOs: 1 or 3 under at least low stringency conditions. The derivatives of the nucleic acid molecule of the present invention defined herein also includes oligonucleotides, PCR primers, antisense molecules, molecules suitable for use in co-suppression and fusion nucleic acid molecules. Some molecules also contemplated are capable of regulating expression of the Pas n 1 gene.

Derivatives of the protein molecules defined herein include fragments, parts, portions, and variants from natural, synthetic or recombinant sources including fusion proteins. The derivatives include fragments having particular parts of the entire protein fused to peptides, polypeptides or other proteinaceous or non-proteinaceous molecules. Parts or fragments include, for example, active regions of the Pas n 1 protein. Derivatives may be derived from insertion, deletion or substitution of amino acids. Conveniently, these are prepared by first making single or multiple nucleotide substitutions, deletions and/or additions to the encoding nucleic acid. Alternatively, once the amino acid sequence is known, amino acids can be chemically added by established techniques and in any sequence required to give the desired mutant. All such derivatives are encompassed by the present invention.

Amino acid insertional derivatives of Pas n 1 of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with Table 2.

TABLE 2

Suitable residues for amino acid substitutions

| Original Residue | Exemplary Substitutions |
|---|---|
| Ala | Ser |
| Arg | Lys |
| Asn | Gln; His |
| Asp | Glu |
| Cys | Ser |
| Gln | Asn; Glu |
| Glu | Asp |
| Gly | Pro |
| His | Asn; Gln |
| Ile | Leu; Val |
| Leu | Ile; Val |
| Lys | Arg; Gln; Glu |
| Met | Leu; Ile; Val |
| Phe | Met; Leu; Tyr |
| Ser | Thr |
| Thr | Ser |
| Trp | Tyr |
| Tyr | Trp; Phe |
| Val | Ile; Leu; Met |

Where a derivative Pas n 1 is produced by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1-10 amino acid residues and deletions will range from about 1-20 residues. Preferably, deletions or insertions are made in adjacent pairs, i.e. a deletion of two residues and a corresponding insertion of two residues.

Substitutional amino acid variants are those in which at least one residue in the sequence has been removed and a different residue inserted in its place. An example of substitutional amino acid variants are conservative amino acid substitutions. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine. Additions to amino acid sequences include fusions with other peptides, polypeptides or proteins.

Other examples of recombinant or synthetic derivatives of the Pas n 1 protein of the present invention include single or multiple substitutions, deletions and/or additions of any molecule associated with the protein such as carbohydrates, lipids and/or proteins or polypeptides.

For convenience and by way of shorthand notation, reference herein to Pas n 1 includes reference to any derivatives thereof as contemplated above.

Reference to "fragments" includes reference to parts and portions, from natural, synthetic or recombinant sources including fusion proteins. Parts or fragments include, for example, active regions of Pas n 1.

In one embodiment, said derivatives or fragments are functional fragments.

It is possible to modify the structure of a protein according to the invention for various purposes such as for increasing solubility, enhancing therapeutic or preventative efficacy, enhancing stability or increasing resistance to proteolytic degradation. A modified protein may be produced in which the amino acid sequence has been altered, such as by amino acid substitution, deletion or addition, to modify immunogenicity and/or reduce allergenicity. Similarly components may be added to the protein of the invention to produce the same result.

The protein of the invention may also be modified to incorporate one or more polymorphisms resulting from natural allelic variation and D-amino acids, non-natural amino acids or amino acid analogues may be substituted into the protein to produce modified proteins which fall within the scope of the invention. Proteins may also be modified by conjugation with polyethylene glycol (PEG) by known techniques. Reporter groups may also be added to facilitate purification and potentially increase solubility of the protein according to the invention. Other well known types of modification including insertion of specific endoprotease cleavage sites, addition of functional groups or replacement of hydrophobic residues with less hydrophobic residues as well as site-directed mutagenesis of DNA encoding the protein of the invention may also be used to introduce modifications which could be useful for a wide range of purposes. The various modifications to protein according to the invention which have been mentioned above are mentioned by way of example only and are merely intended to be indicative of the broad range of modifications which can be effected.

In addition to recombinant production of peptides according to the invention, the nucleic acids may be utilised as probes for experimental or purification purposes.

Yet another aspect of the present invention therefore provides a method for identifying a Pas n 1 nucleic acid molecule or a fragment or derivative thereof.

In one embodiment, said method comprises contacting genomic DNA, mRNA or cDNA with a hybridisation effective amount of a Pas n 1 probe and then detecting said hybridisation. The genetic sequence of interest may be in a recombinant form, in a virus particle, bacteriophage particle, yeast cell, animal cell, or a plant cell. Preferably, the genetic sequence originates from Bahia grass.

Preferably, the Pas n 1 probe comprises a sequence of nucleotides of at least 10, 20, 30, 40 or 50 nucleotides, although the use of larger probes are also contemplated in the present invention, derived from the nucleotide sequence set forth in SEQ ID NO: 1 or 3 or its complement or a functional fragment or derivative thereof. Preferably, this sequence is labelled with a reporter molecule capable of giving an identifiable signal (e.g. a radioisotope such as P or S or a biotinylated molecule).

An alternative embodiment of the present invention provides a method for identifying a Pas n 1 genetic sequence or a fragment or derivative thereof comprising contacting two non-complementary nucleic acid "primer molecules" of at least 12 nucleotides in length derived from the nucleotide sequence of the Pas n 1 gene with a nucleic acid template molecule comprising nucleotide sequences related to the primer molecule sequences and amplifying specific nucleic acid molecule copies of the template molecule in an amplification reaction.

In one example, the first primer molecule is preferably derived from the sense strand of the Pas n 1 gene and in particular from the nucleotide sequence set forth in SEQ ID NOs: 1 or 3 or a fragment or derivative thereof and the second primer molecule is preferably derived from the antisense strand of the Pas n 1 and in particular from the complement of the nucleotide sequence set forth in SEQ ID NOs:1 or 3 or a fragment or derivative thereof. Accordingly, both primers hybridise to said template molecule such that, in the presence of a DNA polymerase enzyme, a cofactor and appropriate substrate, DNA synthesis occurs in the 5' to 3' direction from each primer molecule towards the position on the DNA where the other primer molecule is hybridised, thereby amplifying the intervening DNA.

The nucleic acid primer molecule may further consist of a combination of any of the nucleotides adenine, cytosine, guanine, thymidine, or inosine, or functional analogues or derivatives thereof, capable of being incorporated into a polynucleotide molecule provided that it is capable of hybridising under at least low stringency conditions to the nucleic acid molecule set forth in SEQ ID NOs:1 or 3.

The nucleic acid primer molecules may further be each contained in an aqueous pool comprising other nucleic acid primer molecules. More preferably, the nucleic acid primer molecule is in a substantially pure form.

The nucleic acid template molecule may be in a recombinant form, in a virus particle, bacteriophage particle, yeast cell, animal cell, or a plant cell. Preferably, the related genetic sequence originates from Bahia grass pollen.

Still another aspect of the present invention is directed to antibodies to Pas n 1 protein or nucleic acid molecules including catalytic antibodies or derivatives, homologues, or mutants, of said antibodies. Such antibodies may be monoclonal or polyclonal and may be selected from naturally occurring antibodies to Pas n 1 or may be specifically raised to Pas n 1. In the case of the latter, Pas n 1 may first need to be associated with a carrier molecule. The antibodies and/or recombinant Pas n 1 of the present invention are particularly useful as therapeutic or diagnostic agents. Alternatively, fragments of antibodies may be used such as Fab fragments or Fab'$_2$ fragments. Furthermore, the present invention extends to recombinant and synthetic antibodies and to antibody hybrids. A "synthetic antibody" is considered herein to include fragments and hybrids of antibodies. Pas n 1 can also be used to screen for naturally occurring antibodies to Pas n 1.

Both polyclonal and monoclonal antibodies are obtainable by immunization with Pas n 1 or derivative, fragment or mutant thereof and either type is utilizable for immunoassays. The methods of obtaining both types of sera are well known in the art. Polyclonal sera are less preferred but are relatively easily prepared by injection of a suitable laboratory animal with an effective amount of Pas n 1, or antigenic part thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495-499, 1975; *European Journal of Immunology* 6: 511-519, 1976).

Preferably, the antibody of the present invention specifically binds Pas n 1 or derivative, fragment or mutant thereof. By "specifically binds" is meant high avidity and/or high affinity binding of an antibody to a specific antigen. Antibody binding to its epitope on this specific antigen is stronger than binding of the same antibody to any other epitope, particularly those that may be present in molecules in association with, or in the same sample, as the specific antigen of interest. Antibodies that bind specifically to a polypeptide of interest may be capable of binding other polypeptides at a weak, yet detectable, level. Such weak binding, or background binding, is readily discernible from the specific antibody binding to the polypeptide of interest, e.g. by use of appropriate controls.

An antibody as hereinbefore defined is also useful in purifying the Pas n 1 of the present invention. Methods for the affinity purification of proteins using antibodies are well-known to those skilled in the art.

Without limiting the present invention to any one theory or mode of action, and as discussed hereinbefore, Pas n 1 is a major Group I pollen allergen from Bahia grass which is capable of triggering aberrant, unwanted or otherwise inappropriate immune response in subjects hypersensitive to grass pollen allergens, leading to conditions such as but not limited to allergic rhinitis or seasonal asthma. It can also induce hypersensitivity in individuals exhibiting a predisposition in this regard. Accordingly, the identification and sequencing of Pas n 1 has now facilitated the development of a range of diagnostic and prophylactic or therapeutic treatment protocols for use with respect to Pas n 1 related conditions. Also facilitated is the development of reagents for use therein. Accordingly, the present invention should be understood to extend to the use of the Pas n 1 protein, nucleic acid molecule or antibody disclosed herein or a fragment, derivative, or mutant thereof in the therapeutic and/or prophylactic treatment of patients and in the context of diagnostic application.

Methods of treatment include, but are not limited to, administration of the subject proteins or fragments or derivatives thereof to a patient as a means of desensitising or inducing immunological tolerance to Pas n 1 or Pas n 1-like molecules. This may be achieved, for example, by inducing Pas n 1 directed Th2 anergy or apoptosis. Such treatment may be based, for example, on the administration of specific concentrations of a given protein in accordance with a specific regime in order to induce tolerance. Such methodology may eliminate Pas n 1 hypersensitivity or it may reduce the severity of Pas n 1 hypersensitivity.

Accordingly, in another aspect the present invention provides a method for the treatment and/or prophylaxis of a subject, said method comprising administering to said subject an effective amount of a Pas n 1 protein or nucleic acid molecule or an antibody directed to Pas n 1 as hereinbefore defined or a fragment or derivative thereof.

In one embodiment, said subject is treated for a condition characterised by an aberrant, unwanted or otherwise inappropriate immune response to Pas n 1.

Reference to an "aberrant, unwanted or otherwise inappropriate" immune response should be understood as a reference to any form of physiological activity which involves the activation and/or functioning of one or more immune cells where that activity is inappropriate in that it is of an inappropriate type or proceeds to an inappropriate degree. It may be aberrant in that according to known immunological principals it either should not occur when it does so or else should occur when it does not do so. In another example, the immune response may be inappropriate in that it is a physiologically normal response but which is unnecessary and/or unwanted, such as occurs with respect to hypersensitivity responses to innocuous allergens. Preferably said immune response is hypersensitivity to a grass pollen of the family Pancoideae and even more preferably to Bahia grass pollen hypersensitivity or hypersensitivity to immunologically cross-reactive grass pollens of the family Pancoideae or Pooideae.

Reference to "Bahia grass pollen hypersensitivity" should be understood to mean the exhibition of clinical symptoms of IgE mediated Bahia grass pollen hypersensitivity, for example rhinitis and/or asthma with confirmation of Bahia grass specific IgE as determined via skin prick tests to Bahia grass pollen extract (wheal diameters≤5 mm) and/or using the Kallestad Allercot EAST system (Sanofi-Pasteur Diagnostics, USA) East Score≤3 or other suitable assay for determining allergen specific IgE, such as CAP, Pharmacia. Reference to other Pancoideae subfamily grass pollen hypersensitivities should be understood to have an analogous definition in terms of these IgE mediated symptoms.

Without limiting the present invention in any way, subjects presenting with hypersensitivity to Bahia grass pollen may also present with hypersensitivity to other grass pollens such as not limited to those of Timothy, Bermuda or Rye grass. Accordingly, for immunotherapy it may be desirable to administer Pas n 1 in combination with Group I pollen allergens from other grass pollens.

An "effective amount" means an amount necessary at least partly to attain the desired immune response, or to delay the onset or inhibit progression or halt altogether, the onset or progression of a particular condition being treated.

The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials.

The subject of the treatment or prophylaxis is generally a mammal such as but not limited to human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Preferably the mammal is a human or primate. Most preferably the mammal is a human.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

Administration of a peptide or antibody of the present invention (herein referred to as "agent") in the form of a pharmaceutical composition, may be performed by any convenient means. The agent of the pharmaceutical composition is contemplated to exhibit therapeutic activity when administered in an amount which depends on the particular case. The variation depends, for example, on the human or animal and the agent chosen. A broad range of doses may be applicable. Considering a patient, for example, from about 0.1 mg to about 1 mg of an agent may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation.

The agent may be administered in a convenient manner such as by the oral, intravenous (where water soluble), intraperitoneal, intramuscular, subcutaneous, intradermal, intranasal, sublingual or suppository routes or implanting (e.g. using slow release molecules). The agent may be administered in the form of pharmaceutically acceptable non-toxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

In accordance with these methods, the agent defined in accordance with the present invention may be coadministered with one or more other compounds or molecules. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of molecules. These molecules may be administered in any order.

Another aspect of the present invention contemplates the use of a Pas n 1 protein or nucleic acid molecule or an antibody directed to Pas n 1 as hereinbefore defined in the manufacture of a medicament for the treatment of a condition in a mammal.

Yet another aspect of the present invention is directed to the use of a Pas n 1 protein or nucleic acid molecule or an antibody directed to Pas n 1 as hereinbefore defined for therapy or prophylaxis.

In yet another further aspect, the present invention contemplates a pharmaceutical composition comprising a molecule as hereinbefore defined and one or more pharmaceutically acceptable carriers and/or diluents. Said agents are referred to as the active ingredients.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The pharmaceutical composition may also comprise genetic molecules such as a vector capable of transfecting target cells where the vector carries a nucleic acid molecule encoding said molecule. The vector may, for example, be a viral vector.

Yet another aspect of the present invention relates to the molecules, as hereinbefore defined, when used in the method of the present invention.

In yet another aspect, the present invention should be understood to extend to the use of the proteins the present invention in diagnostic applications. Said diagnostic applications include, but are not limited to measurement of the reactivity of a subject's cells to Pas n 1. This is of use, for example, with respect to the diagnosis and/or monitoring of conditions characterised by an aberrant, unwanted or otherwise inappropriate immune response to Pas n 1. The proteins may be added into solution or bound to a solid support together with cells derived from peripheral blood or from tissue either unfractionated, fractionated or derived as a continuous cell line. Reactivity to the subject protein may then be measured by standard proliferation assays such as incorporation of $H^3$-thymidine, measurement of expressed or secreted molecules such as surface markers, cytokines or other standard assays of cellular activity which are well known in the art.

One may also seek to screen for the present of Pas n 1 specific antibodies in a biological sample such as a blood sample, or one may seek to screen for Pas n1 itself.

Detecting Pas n 1 may be useful, for example, in terms qualitatively or quantitatively detect Pas n 1 levels. However, these methods may also be utilised to screen for mutations or polymorphisms in Pas n 1 which mutations may result in, for example, aberrant immunogenicity. These methods may be utilised for the purpose of screening for peptide molecules suitable for therapeutically or prophylactically treating an individual.

A variety of methods well known in the art can be used to determine polypeptide or antibody levels either directly or indirectly. Such methods include immunochemical methods, such as western blotting, ELISA, immunoprecipitation, and RIA, gel electrophoresis methods including one and two-dimensional gels, methods based on protein or peptide chromatographic separation or methods that use protein-fusion reporter constructs and colorimetric readouts.

A wide range of immunoassay techniques may be used such as those described in U.S. Pat. Nos. 4,016,043, 4,424, 279 and 4,018,653. These methods may be employed for detecting Pas n 1. By way of example only, an antibody raised against Pas n 1 is immobilised onto a solid substrate to form a first complex and an environmental sample to be tested for the presence of Pas n 1 brought into contact with the bound molecule. After a suitable period of incubation, for a period of time sufficient to allow formation of an antibody-Pas n 1 secondary complex, a second Pas n 1 antibody labelled with a reporter molecule capable of producing a detectable signal is then added and incubated, allowing sufficient time for the formation of a tertiary complex of antibody-Pas n 1-labelled antibody. Any unreacted material is washed away, and the presence of the tertiary complex is determined by observation of a signal produced by the reporter molecule. The results may either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of minor variations will be readily apparent. The antibodies used above may be monoclonal or polyclonal. This method may also be adapted to screen for the presence of antibody in a sample using the protein molecule, or fragments thereof, of the present invention.

By "reporter molecule", as used in the present specification, is meant a molecule which, by its chemical nature, produces an analytically identifiable signal which allows the detection of antigen-bound antibody. Detection may be either qualitative or quantitative. The most commonly used reporter molecule in this type of assay are either enzymes, fluorophores or radionuclide containing molecules (i.e. radioisotopes). In the case of an enzyme immunoassay, an enzyme is conjugated to the second antibody, generally by means of glutaraldehyde or periodate. As will be readily recognised, however, a wide variety of different conjugation techniques exist which are readily available to one skilled in the art. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable colour change. It is also possible to employ fluorogenic substrates, which yield a fluorescent product.

Alternatively, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining complex is then exposed to the light of the appropriate wavelength, the fluorescence observed indicates the presence of the molecule of interest. Immunofluorescence and EIA techniques are both very well established in the art. However, other reporter molecules, such as radioisotope, chemiluminescent or bioluminescent molecules, may also be employed. It will be readily apparent to the skilled technician how to vary the procedure to suit the required purpose.

Accordingly, yet another aspect of the present invention is directed to a method of diagnosing or monitoring a condition in a mammal, which condition is characterised by an aberrant, unwanted or inappropriate response to Pas n 1, said method comprising screening for Pas n 1 T or B cell reactivity.

Still another aspect of the present invention is directed to detecting the presence of Pas n 1 or a fragment or derivative thereof in a sample.

In another embodiment the present invention provides diagnostic kits for use in the methodology hereinbefore defined.

The present invention is further described by reference to the following non-limiting Figures and Examples.

Example 1

Characterisation and Cloning of Pas n 1, the Major Allergen of Bahia Grass Pollen Methods
Patients and Sera Initially, 34 patients presenting to The Alfred Hospital Allergy clinic with seasonal rhinitis, with or without asthma, were skin prick tested (SPT) to determine the frequency of sensitization to a panel of common environmental allergens including BaGP extract. Subsequently, sera collected from 31 additional patients (Table 4) with seasonal rhinitis and BaGP sensitization as detected by SPT were tested for IgE reactivity with BaGP by ImmunoCAP (Phadia, Uppsala, Sweden) and ELISA. Stored sera from another 25 patients with seasonal rhinitis and known serum IgE reactivity to BaGP by ELISA (Davies et al., 2005) were included in the testing of IgE reactivity with rPas n 1. Control sera were obtained from 44 non-atopic donors negative on SPT or ImmunoCAP assays with a panel of environmental aeroallergens, and 15 atopic non-grass pollen allergic donors. Approval was obtained from the Alfred Hospital Ethics Committee with informed written consent from each serum donor.

SDS-PAGE, Protein and Carbohydrate Staining and Immunoblotting

Bahia grass (*P. notatum*) and ryegrass (*Lolium perenne*) pollen (Greer Laboratories, Lenoir N.C., USA) proteins were extracted in phosphate buffered saline (PBS) and clarified by centrifugation. The BaGP extract was separated by 12% sodium dodecyl sulfate polyacrylamide gel electrophoresis (SDS-PAGE) and stained with Coomassie Brilliant Blue R250 (CBB) for protein or Pro Q Emerald 300 stain for glycoprotein (Molecular Probes, Oreg., USA). Alternatively, proteins were transferred from the gel to nitrocellulose and tested for mAb FMC-A1 (Smart et al., 1983) and serum IgE reactivity (Davies et al., 2005).

2D Gel Electrophoresis and Immunoblotting

*Paspalum notatum* pollen (Greer Laboratories) was solubilized in PBS and clarified by centrifugation. 250 μg of extract dialysed against ultrapure water was separated by isoelectric focusing across 13 cm IPG dry gel strips with a linear pH gradient from 3 to 10 on Pharmacia Multiphor II according to the manufacturer's instructions. Focused gel strips were loaded onto 14 or 16% SDS-PAGE 20 cm slab gels and electrophoresed with tris-glycine buffers in BioRad Protean II system as instructed. Gels were stained with Coomassie Brilliant Blue or transferred to PVDF membranes in a BioRad transblot II cell with 150 mM sodium phosphate buffer, pH 6.8 at 20V overnight, 12° C. The membrane was either stained with Coomassie Brilliant Blue or blocked in 5% skim milk powder in PBS with 0.05% Tween 20 (MP/PBST) and probed with mAb FMC-A1 culture supernatant (Smart et al., 1983) diluted 1/10 for 90 min. MP/PBST was used for all antibody dilutions. The mAb reactivity was detected using goat anti-mouse Ig-horse radish peroxidase (HRP) (Silenus) and visualized with chloronapthol and hydrogen peroxide development. Similarly, immunoblots prepared from 125 μg of dialysed extract focused on 7 cm pH 3-10 IPG dry strip gels and resolved on 14% SDS-PAGE mini-gels were blocked and probed with human sera diluted 1/5 overnight at 4° C. IgE reactivity was detected with rabbit anti-IgE diluted 1/1000 followed by goat anti-rabbit Ig-HRP at 1/1000 (Promega). The amino terminal residues of the protein spots were sequenced by Edman degradation by Australian Proteome Analysis Facility.

Molecular Cloning

RNA was prepared from *P. notatum* pollen using a Mini Plant RNA extraction kit (Qiagen, Calif., USA). The group 1 allergen cDNA was amplified by a two-step method for rapid amplification of cDNA ends (RACE) (Invitrogen, Calif., USA). Firstly, a partial Pas n 1 cDNA product was amplified by 3' RACE using Platinum Pfx polymerase (Invitrogen) an oligonucleotide primer based on the N-terminal peptide sequence and incorporating the conserved NIT peptide motif of group 1 allergens (GGGC-CCCCGAAGGTGGCNCCCGGCAARAACATCAC (SEQ ID NO:11), where R=A or G and N=A, G, C or T). Amplification products were cloned into pCR4-Blunt with topoisomerase (Invitrogen) and transformed into *Escherichia coli* Top10 (Invitrogen). DNA sequencing of recombinant plasmids was performed at the Baker Heart Research Center (Melbourne, Australia). Secondly, the 5' untranslated region of the Pas n 1 cDNA through the coding region until the TAG stop codon was amplified by two-step nested 5' RACE using primers determined from the sequence of the 3' RACE products (5' RACE primer; CGGATCAAGTGCAT-GCGCATGATGCATGG (SEQ ID NO;12), nested 5' RACE primer; GAAACAAGTCGATCTAGAACTGGACGTTGG (SEQ ID NO:13) and cloned in the same manner.

Sequence Analysis

Sequences were analysed using BLAST and BESTFIT within the Australian Genome Information Service. Clustal W was utilized with the Blosum 30 matrix and penalties for gap opening of 10 and extension of 0.5 to align the peptide sequence of Pas n 1 with a representative beta expansin isoform from each species identified in the top 50 hits of a BLAST search of the SwissProt database (Thompson et al., 1994). The multiple alignment file was analysed using ProtDist using a Kimura model of the Dayhof PAM matrix and the universal genetic code (Felsenstein, 1989). A phylogenetic tree was generated by Neighbor (Felsenstein, 1989).

Subcloning and Protein Expression

The cDNA of Pas n 1 encoding the mature peptide was amplified and directionally subcloned into the pET-28a protein expression vector (Novogen Merck, Darmstadt, Germany) encoding an N-terminal hexahistidine purification tag using primers with either 5' NheI or 3' HindIII sites (BG1petFor: TATATTCATATGGGCCCCCCCAAGGTGC-CGCCCGGCCCC (SEQ ID NO:14) and BGl petRev: GCT- TGCAAGCTTCTAGAACTGGACGTTGGAATTG (SEQ ID NO:15)). rPas n 1 was produced in *E. coli* BL21 (DE3) RIPL (Stratagene, Ceder Creek, Tex., USA) and purified under denaturing conditions on a Ni-NTA affinity column (Qiagen). Crude cells lysates and purified rPas n 1 were resolved by 12% SDS-PAGE and blots were probed with hexahistidine antiserum (Roche, Penzberg, Germany) and mAb FMC-A1.

Serum IgE Reactivity with Recombinant Pas n 1

The capacity for rPas n 1 (1 and 5 µg), in comparison with a control irrelevant allergen from rubber latex, rHev b 6.01 (1 and 5 µg) (Drew et al., 2004), to inhibit serum (diluted 1 in 5) IgE reactivity with BaGP extract by immunoblotting, and with BaGP and ryegrass pollen extracts by ELISA, was tested. Serum IgE reactivity with rPas n 1 coated at 10 µg/ml on microtiter plate wells was tested by ELISA (Davies et al., 2005). The IgE reactivity of each serum was expressed as the number of standard deviations above the mean for the non-atopic sera tested in each assay. The mean OD value and standard deviation for the 19 non-atopic sera in the first assay were 0.170 and 0.099 units, respectively and for the 25 additional non-atopic sera in the second assay were 0.098 and 0.051 units. Six BaGPallergic sera and five non-atopic sera were tested in both assays showing an inter-assay correlation of 99%. The correlation between IgE reactivity of the BaGP-allergic sera with BaGP extract versus rPas n 1 was determined using Spearman's rank test for paired data.

Basophil Activation Assay rPas n 1, BaGP extract and control rHev b 6.01 were tested at 0.1-10 µg/ml for activation of basophils from whole blood of three BaGP-allergic donors and one atopic non-BaGP-allergic donor based on analysis of upregulation of surface expression of CD63 on IgE-positive basophils by flow cytometry (Drew et al., 2004).

Results

Bahia Grass Pollen is an Important Allergen in Patients with Seasonal Rhinitis

Twenty-nine of 34 consecutive patients (85%) presenting with seasonal rhinitis during one month of spring within the grass pollen season were SPT positive for BaGP. Of the 31 BaGP SPT positive patients with seasonal rhinitis subsequently recruited into the study (Table 4), 17% also had symptoms of asthma and 92, 64 and 60% were also sensitized to ryegrass pollen, Bermuda grass pollen and house dust mite, respectively. Ninety percent of these patients showed serum IgE reactivity with BaGP extract by ELISA (Table 4).

the Major Bahia Grass Pollen Allergens are Glycoproteins

BaGP extract separated according to size by SDS-PAGE showed predominant CBB-stained bands at approximately 29 and 60 kDa. These bands also stained positively for glycoprotein (FIG. 1A). The frequency of IgE reactivity with equivalent 29 and 60 kDa bands of BaGP extract immunoblotted with sera from 21 patients with strong BaGP reactivity by ELISA was 100 and 52%, respectively (Table 4, FIG. 1B). A mAb FMC-A1 to the group 1 allergen of ryegrass pollen, Lol p 1, reacted with the 29 kDa protein band of BaGP (FIG. 1B). Together these data indicate that the 29 kDa glycoprotein is a group 1 allergen of BaGP.

Characterisation of the Group 1 Allergen of Bahia Grass Pollen

BaGP extract was then separated by two-dimensional gel electrophoresis (FIG. 1C). Five protein spots resolved at 29 kDa and were reactive with the mAb FMC-A1 and serum IgE of patient 6 but not serum of a non-atopic donor (FIG. 1D). Four of the spots at 29 kDa had neutral pIs between 6.8 and 7.1 and there was an additional immunoreactive spot at pH 10.

The predominant 29 kDa neutral protein that corresponded to the most reactive spot on the two-dimensional immunoblots was excised from an equivalent membrane (FIGS. 1C and D). The N-terminal peptide sequence was determined as GPPKVAPGK (Table 5). The tenth amino acid blocked the N-terminal sequencing reaction suggesting the presence of a glycosylation site.

Cloning of Pas n 1, the Group 1 Allergen of Bahia Grass Pollen

BaGP RNA was reverse transcribed and used as a template to amplify and clone the group 1 allergen cDNA, including the 3' and 5' untranslated regions, by RACE amplification. From the 3' RACE cloning six clones were identical and from the 5' RACE cloning 10 clones had greater than 99% identity to each other at the nucleotide level, including the untranslated regions. The deduced peptide sequences were identical to each other in the region encoding the mature protein sequence indicating that a single isoform had been amplified and cloned.

Figure 2:
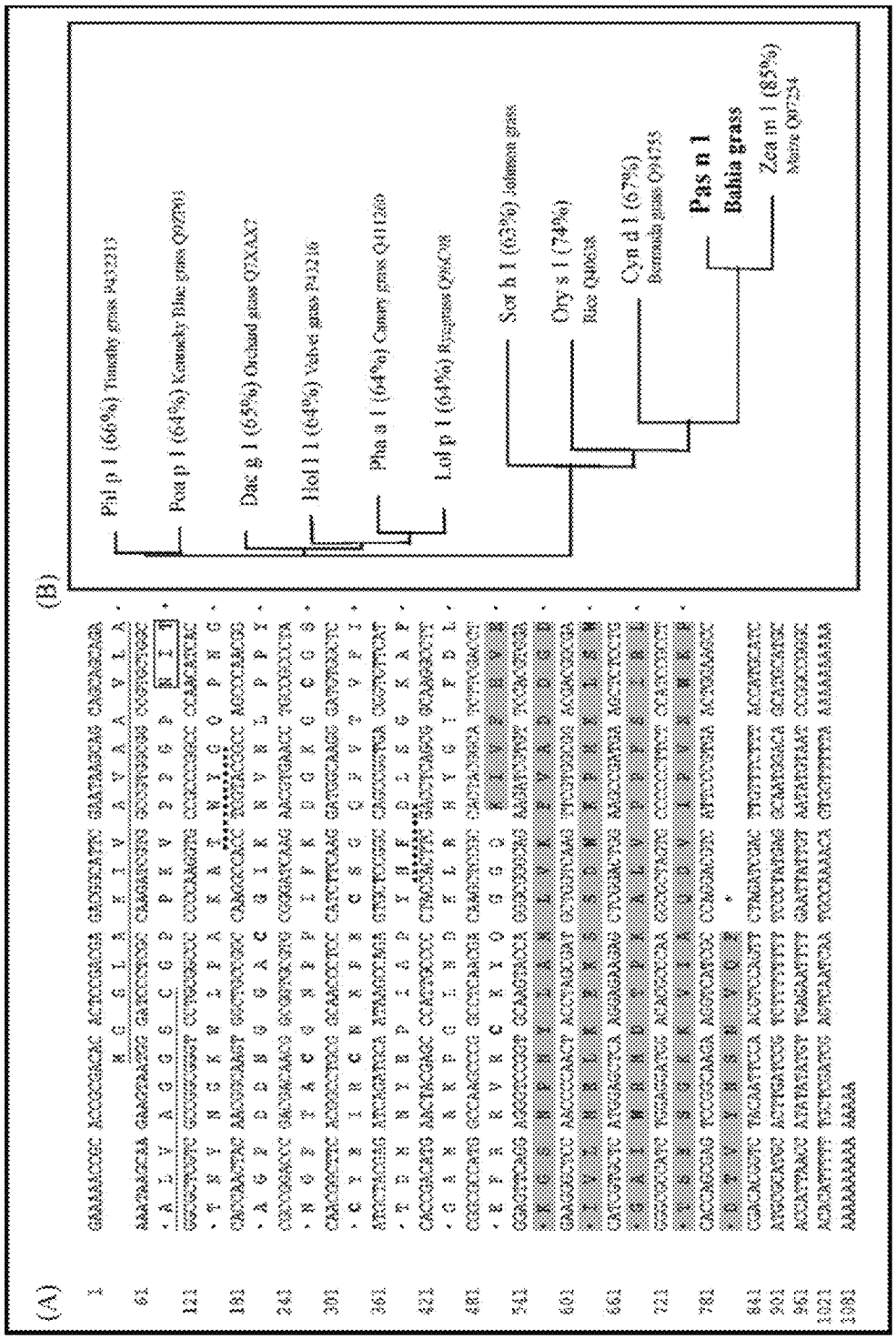
FIG. 2*a* is a schematic representation of the cDNA (SEQ ID NO: 1) and deduced peptide sequence (SEQ ID NO: 2) of Pas n 1. The signal peptide sequence is underlined and the glycosylation site is boxed. The C terminal domain homologous to the group 2 allergen is shaded and features conserved amongst proteins of the grass β expansin family are in italics (HFD and TWYG) or bold (domain 1 cysteines and domain 2 tryptophans).
FIG. 2*b* is a schematic representation of the relationship between the newly cloned Pas n 1 and Group I pollen allergens of other grass species. One representative Group I isoform of each grass species identified by BLAST searches was included. Kentucky bluegrass (Poa p 1), timothy grass (Phl p 1), orchard grass (Dac g 1), velvet grass (Hol l 1), ryegrass (Lol p 1), canary grass (Pha a 1), Bermuda grass (Cyn d 1) and rice (Ory s 1)

The nucleotide sequence of the full length cDNA encoding the putative Pas n 1 was determined and its amino acid sequence deduced (FIG. 2A). The cDNA contains 1095 nucleotides and encodes a protein of 265 amino acids including a putative 23 residue signal peptide sequence. The predicted molecular weight of the mature protein without carbohydrate is 26.7 kDa and the predicted pI is 9.73. This allergen has been designated Pas n 1.0101 by the International Union of Immunological Societies Sub-committee for Allergen Nomenclature.

Relationship of Pas n 1 with Group 1 Pollen Allergens of Other Grass Species

The newly cloned Pas n 1 cDNA has sequence homology with the (β-expansin family of proteins that includes the group 1 grass pollen allergens. Pas n 1 shows greatest similarity to the Panicoideae maize group 1 allergen with identity ranging from 84 to 85% for the four isoforms (Zea m 1 a-d, Li et al., 2003). The group 1 pollen allergens, Lol p 1 and Phl p 1, of the Pooideae temperate grasses ryegrass and Timothy grass, showed 64 and 66% sequence identity with Pas n 1, respectively (FIG. 2B).

Expression of Recombinant Pas n 1

Figure 3:
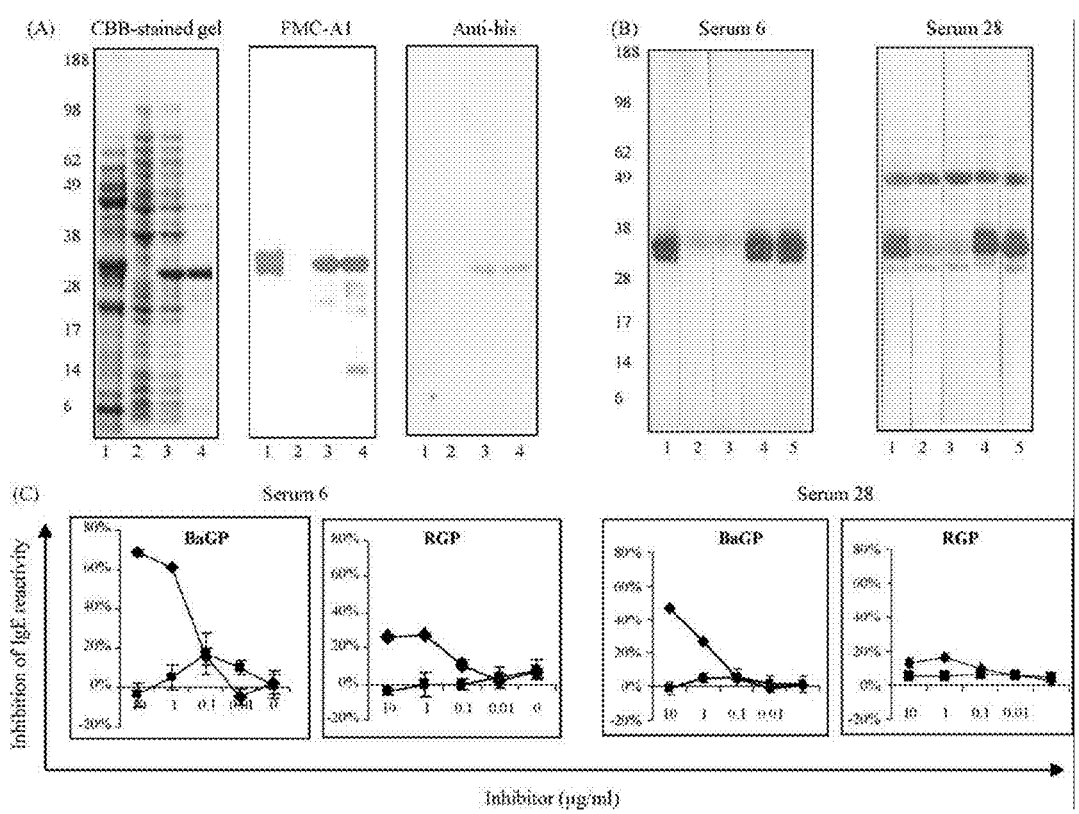
FIG. 3 is and image of the expression of Pas n 1 and graphical representation of the dose-dependent inhibition of serum IgE reactivity. (a) CBB-stained SDS-Page and immunoblots probed with mAb FMC-A1 and anti-hexahisitidine antiserum ((1) BaGP extract; (2) uninduced *E. coli* lysate; (3) induced *E. coli* expressing Pas n 1; (4) purified rPas n 1). (B) Inhibition of serum reactivity with natural Pas n 1 in BaGP extract by rPas n 1 by immunoblotting ((1) uninhibited; (2) rPas n 1 (5 µg); (3) rPas n 1 (1 µg); (4) rHev b 6.01 (5 µg); (5) rHev b 6.01 (1 µg)). (C) Dose-dependent inhibition of serum IgE reactivity with BaGP and ryegrass pollen (RGP) extract by rPas n 1 ELISA (diamond, rPas n 1; Square, rHev b 6.01).

The cDNA encoding the mature protein of Pas n 1 was expressed in *E. coli* transformed with the recombinant pET-28a-Pas n 1 vector. A strong protein band at 27 kDa was induced in the transformed *E. coli* that reacted with mAb FMC-A1 and an antiserum to the hexahistidine purification tag (FIG. 3A, lanes 2-3). The rPas n 1 was purified from the transformed *E. coli* lysate using metal affinity chromatography (FIG. 3A, lane 4).

IgE Reactivity with Recombinant Pas n 1

Purified rPas n 1 but not an irrelevant negative control allergen, rHev b 6.01, inhibited the IgE reactivity of patient sera 6 and 28 with the 29 kDa allergen band of BaGP extract (FIG. 3B, left panel). Notably, rPas n 1 specifically inhibited IgE reactivity of patient serum 28 with the group 1 allergen band and not the 60 kDa allergen band (FIG. 3B, right panel). This inhibition by rPas n 1 of IgE reactivity with BaGP was dose-dependent and achieved a maximum inhibition of 79% for serum 6 and 47% for serum 28, which also had IgE reactivity was against other allergens of BaGP (FIG. 3C). rPas n 1 inhibited 27% of serum 6 IgE reactivity with ryegrass pollen but did not inhibit serum 28 IgE reactivity with ryegrass pollen (FIG. 3C).

Figure 4:
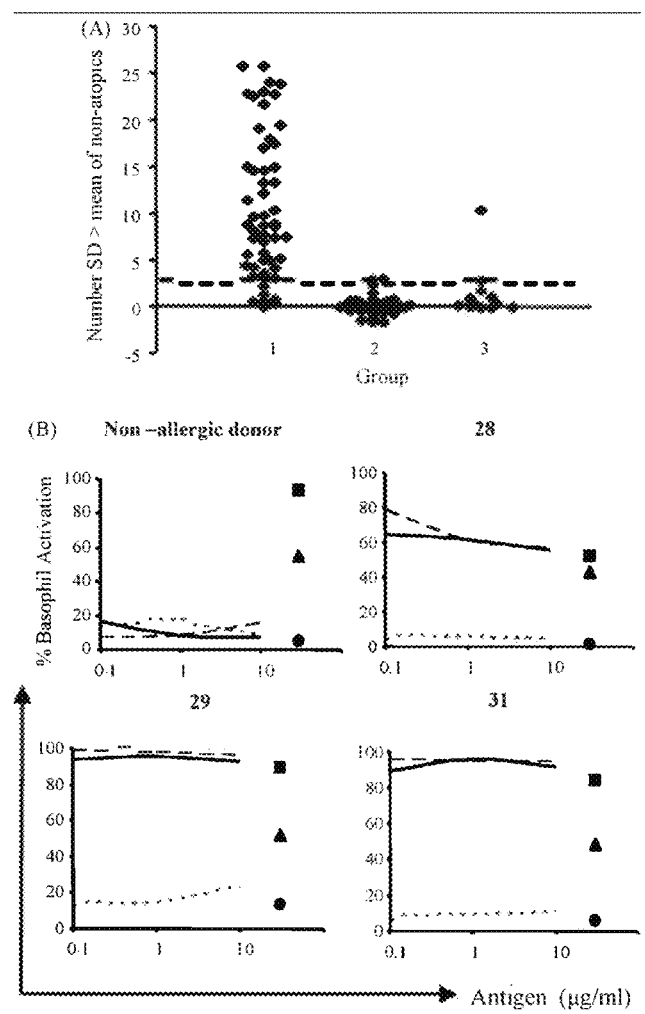
FIG. 4 is a graphical representation of rPas n 1 IgE reactivity. (A) ELISA ((group 1) BaGP-allergic (n=55); (2) non-atopic (n=44); (3) atopic non-grass allergic (n=15); cut-off, dotted line). (B) Basophil activation for one atopic non-grass pollen-allergic and three BaGP-allergic subjects (BaGP, solid line; rPas n 1, dashed line; rHev b 6.01, dotted line; (filled square) anti-huIgE; (filled triangle) fMetLeuPhe; (filled circle) no stimulus).
Figure 5:
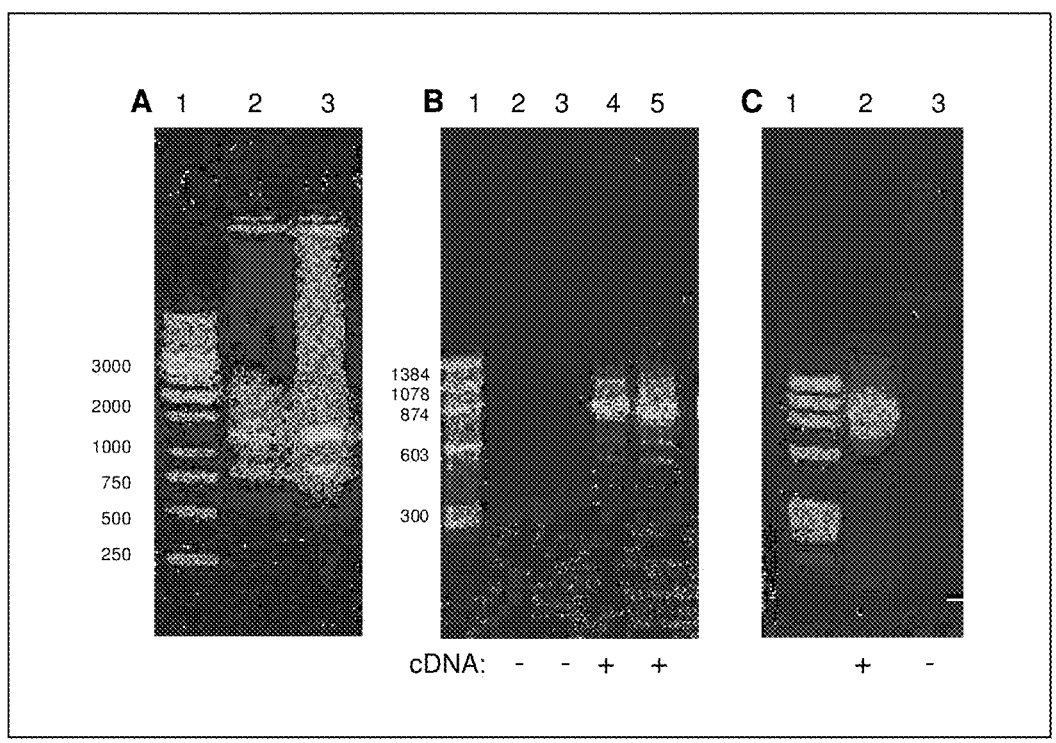
FIG. 5 in an image of the expression of recombinant Pas n 1. Immunoblots of crude bacterial lysates probed with anti-MBP serum (A) and FMC-A1 monoclonal antibody to Lol p 1 (B). Lane 1 Bahia grass pollen extract, 2 uninduced cell lysate, 3 induced empty pMAL-c2X vector, 4 induced pMAL-c2x-Pas n 1 with cytoplasmic expression, 5 induced pMAL-p2x-Pas n 1 with periplasmic expression.

Sera of 30 of the 31 BaGP-allergic subjects described in Table 1 and a second panel of 25 grass pollen-allergic patients with known IgE reactivity to BaGP by ELISA, showed an overall frequency of IgE reactivity with rPas n 1 by ELISA in 47 of 55 (85%) based on a cut-off of three standard deviations above the mean of non-atopic sera (FIG. 4A). Only one of 15 atopic non-grass pollen-allergic donors showed IgE reactivity with rPas n 1. Serum IgE reactivity with rPas n 1 and BaGP (data not shown) was well correlated in the BaGP-allergic group (r=0.85, p<0.001).

BaGP extract and rPas n 1 but not rHev b 6.01 upregulated surface CD63 expression on basophils from all of three BaGP-allergic donors tested and not basophils from a control atopic non-grass pollen-allergic donor with house dust mite allergy (FIG. 4B). The positive control stimuli, fMetLeuPhe and anti-human IgE antibodies, activated the basophils from all donors including the control donor.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Baldo B. A. (1983), Standardization of allergens, examination of existing procedures and the likely impact of existing procedures and the likely impact of new techniques on the quality control of extracts, *Allergy*, 38: 535-546.

Chase A. (1995), Revision of the Hitchcocks Manual of Grasses of the United States, *US Dept Agriculture Miscel Publication* 200, p 605.

Felsenstein, J. (1989), PHYLIP-Phylogeny Inference Package (Version 3.2). *Cladistics* 5: 164-166.

King T. P. (1976), Chemical and biological properties of some atopic allergens, *Adv Immunol*, 23: 77-105.

King and Norman (1962), Isolation studies of allergens from ragweed pollen, *Biochemistry*, 1: 709-720.

Matin B. G. et al. (1985), Cross-allergenicity among the grasses, *Ann Allergy*, 54: 99-104.

Petersen A. et al. (1993), Characterisation of grass Group II allergens in timothy grass pollen, *J. Allergy Clin. Immunol.*, 92: 789-796.

Phillip J. W. et al. (1979), Bahia grass pollen—an important aeroallergen, *J. Allergy Clin Immunol*, 63: 192-193.

Sweeny M. et al. (1994), Immunodetection and comparison of Melaluca, Bottlebrush, and Bahia pollens, *Int Arch Allergy Appl Immunol*, 105: 289-296.

Thompson et al. (1994), CLUSTAL W: Improving the sensitivity of progressive multiple sequence alignment through sequence weighting, position-specific gap penalties and weight matrix choice, *Nucleic Acids Research*, 22: 4673-4680.

Tovey and Baldo (1987), Characterization of allergens by protein blotting, *Electrophoresis*, 8: 452-463.

TABLE 3

Primer sequences used for amplification and cloning Pas n 1

| | | |
|---|---|---|
| BG1for1 | (SEQ ID NO: 5) | Gggccccgaaggtggcncccggc aaraacatcac* |
| BG1for2 | (SEQ ID NO: 6) | gggccccgaaggtggcncccggc |
| BG1rev1 | (SEQ ID NO: 7) | ggtgcctccctcggtagtgaggcg gacgg |
| BG1rev2 | (SEQ ID NO: 8) | cccttcttggccatggcgccgaac gc |
| BG1rev4 | (SEQ ID NO: 9) | cggatcaagtgcatgcgcatgatg catgg |
| BG1rev6 | (SEQ ID NO: 10) | gcttgc<u>aagctt</u><b>cta</b>gaactggac gttggaattg |

*degenerate nucleotides r = ag and n = agct

TABLE 4

IgE reactivity of Bahia grass pollen-allergic patients

| Subject number | Sex | Diagnosis | BaGP ELISA (OD 495 mm)[a] | BaGP SPT (mm diameter) | BaGP ImmunoCAP (kU/I) | BaGP IgE Immunoblot[b] | | Other sensitivities |
|---|---|---|---|---|---|---|---|---|
| | | | | | | 29 kDa | 60 kDa | |
| 1 | m | SR | 0.37 | 12 | 0.93 | | | R, Be |
| 2 | f | SR | 0.15 | 6 | 0.69 | | | R, Be, HDM |
| 3 | m | SA, SR | 1.29 | 11 | 8.89 | +/− | +++ | R, Be, HDM, C |
| 4 | m | SA, SR | 0.91 | 14 | 3.31 | + | − | R, Be |
| 5 | m | SA, SR | 0.16 | 7 | 0.51 | | | R, Be |
| 6 | f | SA, SR | 1.53 | 10 | 28.10 | +++ | − | R, Be, C |
| 7 | m | SR | 0.55 | 14 | 8.97 | ++ | − | R, Be |
| 8 | m | SR | 1.64 | 8 | 21.30 | ++ | − | R, Be, HDM, C |
| 9 | f | SR | 0.45 | 10 | 5.54 | | | R, Be, HDM, C |
| 10 | m | SR | 1.26 | 12.5 | 14.00 | + | + | R, Be, HDM |
| 11 | m | SR | 1.20 | 8 | 16.40 | + | − | R, Be, HDM, C |
| 12 | f | SR | 0.72 | 15 | 7.00 | NT | | R, Be |
| 13 | m | SR | 0.85 | 9 | 8.28 | ++ | + | R, Be, HDM, C |
| 14 | m | SR | 0.32 | 9 | 1.97 | | | R, Be |
| 15 | f | SR | 0.50 | 15 | 4.68 | ++ | + | R, Be, HDM, C |
| 16 | f | SA, SR | 1.11 | 6 | 9.89 | + | ++ | R, Be, C |
| 17 | f | SR | 1.07 | 0.5 | 12.30 | +++ | +/− | R, Be, C |
| 18 | m | SR | 1.04 | 8 | 5.29 | ++ | − | R, Be |

TABLE 4-continued

IgE reactivity of Bahia grass pollen-allergic patients

| Subject number | Sex | Diagnosis | BaGP ELISA (OD 495 mm)[a] | BaGP SPT (mm diameter) | BaGP ImmunoCAP (kU/l) | BaGP IgE Immunoblot[b] 29 kDa | 60 kDa | Other sensitivities |
|---|---|---|---|---|---|---|---|---|
| 19 | m | SR | 0.30 | 5 | 0.91 | | | R, Be, HDM, C |
| 20 | m | SR | 1.61 | 10.5 | 38.30 | ++ | − | R, Be |
| 21 | m | SR | 0.44 | 8 | 3.35 | | | R, Be |
| 22 | m | SR, AR | 0.28 | 7 | 1.99 | | | R, Be, HDM, C |
| 23 | m | SR | 0.39 | 13 | 1.76 | | | R, Be |
| 24 | m | SR | 1.57 | 8 | 23.10 | + | − | R, Be, HDM, C |
| 25 | m | SR | 0.77 | 6 | 3.07 | + | − | R, Be, HDM |
| 26 | m | SR | 0.62 | 9 | 6.53 | +/− | + | R, Be, HDM, C |
| 27 | m | SR | 0.91 | 11 | 18.20 | +/− | ++ | R, Be, HDM, C |
| 28 | f | SR | 2.03 | 11 | 38.50 | ++ | ++ | R, Be |
| 29 | f | SR | 0.55 | 7 | 3.86 | + | − | R, Be |
| 30 | f | SR | 0.45 | 6 | 1.36 | + | +/− | R, Be, HDM |
| 31 | f | SA, SR | NT | 7 | 9.46 | + | +/− | R, Be, C |

[a]Cut-off for positive (three stantdard deviation above the mean of 12 non-atopic controls) was 0.32 optical density (OD) units.
[b]Sera with BaCP ELISA OD < 0.45 were tested by IgE, immunoblotting;
R, ryegrass pollen;
Be, Bermuda grass pollen;
HDM, house dust mite;
C, cat dander;
NT, not tested;
SR, seasonal thinitis;
SA, seasonal asthma.

TABLE 5

Alignment of N-terminal sequence of BaGP group 1 allergen with other grass pollen group 1 allergen sequences.

| Allergen | Peptide sequence | |
|---|---|---|
| Pas n 1 (N-terminal peptide) | GPPKVAPGK [c] | (SEQ ID NO: 16) |
| Pas n 1 (deduced sequence) | GPPKVPPGPNIT | (SEQ ID NO: 17) |
| Sor h 1 [b] | GPPKVAPGKNIT | (SEQ ID NO: 18) |
| Zea m 1 [c] | GPPKVPPGPNIT | (SEQ ID NO: 19) |
| Cyn d 1 [c] | AMGDKPGPNIT | (SEQ ID NO: 20) |
| Lol p 1 [c] | IAKVPPGPNIT | (SEQ ID NO: 21) |
| Phl p 1 [c] | IPKVPPGPNIT | (SEQ ID NO: 22) |

[a] Identical amino acids are in bold type.
[b] Sequence from reference (Avjioglu et al., 1993).
[c] Sequences derived from SwissProt-TrEMBL. See FIG. 2B for codes.

The invention claimed is:

1. A pharmaceutical composition comprising an effective amount of a non-glycosylated polypeptide that comprises the amino acid sequence as set forth in SEQ ID NO: 4, or an amino acid sequence having at least 95%, 96%, 97%, 98% or 99% or more sequence identity to the entire amino acid sequence of SEQ ID NO: 4; and an acceptable carrier and/or diluent.

2. A method for the treatment and/or of a grass pollen hypersensitivity in a mammal said method comprising administering to said mammal a pharmaceutical composition comprising an effective amount of a non-glycosylated polypeptide that comprises the amino acid sequence set forth in SEQ ID NO:4, or an amino acid sequence having at least 95%, 96%, 97%, 98% or 99% or more sequence identity to the entire amino acid sequence of SEQ ID NO:4; and an acceptable carrier and/or diluent.

3. The method according to claim 2 wherein said mammal is treated for a condition characterized by an aberrant, unwanted or otherwise inappropriate immune response to Pas n 1.

4. The method according to claim 3 wherein said condition is Bahia grass pollen hypersensitivity.

5. The method according to claim 4 wherein said condition is hypersensitivity to the pollen of grasses of the family Pancoideae or Pooideae.

6. The method according to claim 5 wherein said grass is Timothy, Bermuda or Rye.

7. The method according to claim 6 wherein said polypeptide is administered in combination with one or more Group 1 pollen allergens from other grass pollens.

* * * * *

SEQUENCE LISTING

```
<160> NUMBER OF SEQ ID NOS: 33

<210> SEQ ID NO 1
<211> LENGTH: 1106
<212> TYPE: DNA
<213> ORGANISM: paspalum notatum

<400> SEQUENCE: 1 gaaaaccgc accgcgacac actccgacga gacggcattc gaataagcag cagcagcaga      60
aaataagcaa gaagtaatgg gatccctcgc caagatcgtg gccgtggcgg ccgtgctggc     120
ggcgctcgtc gccggcgggt cctgcggccc ccccaaggtg ccgcccggcc ccaacatcac     180
caccaactac aacggcaagt ggctgccggc caaggccacc tggtacggcc agcccaacgg     240
cgccggaccc gacgacaacg gcggtgcgtg cgggatcaag aacgtgaacc tgccgcccta     300
caacggcttc acggcctgcg gcaacccctc catcttcaag gatggcaagg gatgtggctc     360
atgctacgag atcagatgca ataagccaga gtgctccggc cagccggtga cggtgttcat     420
```

```
caccgacatg aactacgagc ccattgcccc ctaccacttc gacctcagcg gcaaggcctt    480
cggcgccatg gccaagcccg gcctcaacga caagctccgc cactacggca tcttcgacct    540
ggagttcagg agggtccggt gcaagtacca gggcgggcag aagatcgtgt tccacgtgga    600
gaagggctcc aacccccaact acctagcgat gctggtcaag ttcgtggcgg acgacggcga    660
```
<br>(Note: reproduced as shown)

```
caccgacatg aactacgagc ccattgcccc ctaccacttc gacctcagcg gcaaggcctt    480
cggcgccatg gccaagcccg gcctcaacga caagctccgc cactacggca tcttcgacct    540
ggagttcagg agggtccggt gcaagtacca gggcgggcag aagatcgtgt tccacgtgga    600
gaagggctcc aacccccaact acctagcgat gctggtcaag ttcgtggcgg acgacggcga    660
catcgtgctc atggagctca aggagaagag ctcggactgg aagccgatga agctctcctg    720
gggcgccatc tggaggatgg acacgcccaa ggcgctagtg ccccccttct ccatccgcct    780
caccagcgag tccggcaaga aggtcatcgc ccaggacgtc attcccgtga actggaagcc    840
cgacacggtc tacaattcca acgtccagtt ctagatcgac ttgtttcttt accatgcatc    900
atgcgcatgc acttgatccg tctttttttt tccctatgag gcaatggaca gcatgcatgc    960
accattaacc atatatatgt tgagaatttt gaattattgt aatatgtaat ccggccgggc   1020
acacattttt tgctcgatcg agtcaatcaa tgccaaaaca gtggttttta aaaaaaaaaa   1080
aaaaaaaaaa aaaacactg tcatgc                                        1106
```

<210> SEQ ID NO 2
<211> LENGTH: 265
<212> TYPE: PRT
<213> ORGANISM: paspalum notatum

<400> SEQUENCE: 2

```
Met Gly Ser Leu Ala Lys Ile Val Ala Val Ala Val Leu Ala Ala
1               5                  10                  15

Leu Val Ala Gly Gly Ser Cys Gly Pro Pro Lys Val Pro Gly Pro
                20                  25                  30

Asn Ile Thr Thr Asn Tyr Asn Gly Lys Trp Leu Pro Ala Lys Ala Thr
            35                  40                  45

Trp Tyr Gly Gln Pro Asn Gly Ala Gly Pro Asp Asp Asn Gly Gly Ala
        50                  55                  60

Cys Gly Ile Lys Asn Val Asn Leu Pro Pro Tyr Asn Gly Phe Thr Ala
65                  70                  75                  80

Cys Gly Asn Pro Pro Ile Phe Lys Asp Gly Lys Gly Cys Gly Ser Cys
                85                  90                  95

Tyr Glu Ile Arg Cys Asn Lys Pro Glu Cys Ser Gly Gln Pro Val Thr
            100                 105                 110

Val Phe Ile Thr Asp Met Asn Tyr Glu Pro Ile Ala Pro Tyr His Phe
        115                 120                 125

Asp Leu Ser Gly Lys Ala Phe Gly Ala Met Ala Lys Pro Gly Leu Asn
    130                 135                 140

Asp Lys Leu Arg His Tyr Gly Ile Phe Asp Leu Glu Phe Arg Arg Val
145                 150                 155                 160

Arg Cys Lys Tyr Gln Gly Gly Gln Lys Ile Val Phe His Val Glu Lys
                165                 170                 175

Gly Ser Asn Pro Asn Tyr Leu Ala Met Leu Val Lys Phe Val Ala Asp
            180                 185                 190

Asp Gly Asp Ile Val Leu Met Glu Leu Lys Glu Lys Ser Ser Asp Trp
        195                 200                 205

Lys Pro Met Lys Leu Ser Trp Gly Ala Ile Trp Arg Met Asp Thr Pro
    210                 215                 220

Lys Ala Leu Val Pro Pro Phe Ser Ile Arg Leu Thr Ser Glu Ser Gly
225                 230                 235                 240

Lys Lys Val Ile Ala Gln Asp Val Ile Pro Val Asn Trp Lys Pro Asp
                245                 250                 255
```

Thr Val Tyr Asn Ser Asn Val Gln Phe
                260             265

<210> SEQ ID NO 3
<211> LENGTH: 726
<212> TYPE: DNA
<213> ORGANISM: paspalum notatum

<400> SEQUENCE: 3
cctcgccaag atcgtggccg tggcggccgt gctggcggcg ctcgtcgccg gcgggtcctg      60
cggcccccc aaggtgccgc ccggcccaa catcaccacc aactacaacg gcaagtggct     120
gccggccaag gccacctggt acggccagcc caacggcggg gacccgacg acaacggcgg     180
tgcgtgcggg atcaagaacg tgaacctgcc gccctacaac ggcttcacgg cctgcggcaa     240
ccctcccatc ttcaaggatg gcaagggatg tggctcatgc tacgagatca gatgcaataa     300
gccagagtgc tccggccagc cggtgacggt gttcatcacc gacatgaact acgagcccat     360
tgccccctac cacttcgacc tcagcggcaa ggccttcggc ccatggcca gcccggcct     420
caacgacaag ctccgccact acggcatctt cgacctggag ttcaggaggg tccggtgcaa     480
gtaccagggc gggcagaaga tcgtgttcca cgtggagaag ggctccaacc ccaactacct     540
agcgatgctg gtcaagttcg tggcggacga cggcgacatc gtgctcatgg agctcaagga     600
gaagagctcg gactgaaagc cgatgaagct ctcctggggc ccatctgga ggatggacac     660
gcccaaggcg ctagtgcccc ccttctccat ccgcctcacc agcgagtccg gcaagaaggt     720
catcgc                                                                726

<210> SEQ ID NO 4
<211> LENGTH: 242
<212> TYPE: PRT
<213> ORGANISM: paspalum notatum

<400> SEQUENCE: 4

Gly Pro Pro Lys Val Pro Gly Pro Asn Ile Thr Thr Asn Tyr Asn
1               5                   10                  15

Gly Lys Trp Leu Pro Ala Lys Ala Thr Trp Tyr Gly Gln Pro Asn Gly
            20                  25                  30

Ala Gly Pro Asp Asp Asn Gly Gly Ala Cys Gly Ile Lys Asn Val Asn
        35                  40                  45

Leu Pro Pro Tyr Asn Gly Phe Thr Ala Cys Gly Asn Pro Pro Ile Phe
    50                  55                  60

Lys Asp Gly Lys Gly Cys Gly Ser Cys Tyr Glu Ile Arg Cys Asn Lys
65                  70                  75                  80

Pro Glu Cys Ser Gly Gln Pro Val Thr Val Phe Ile Thr Asp Met Asn
                85                  90                  95

Tyr Glu Pro Ile Ala Pro Tyr His Phe Asp Leu Ser Gly Lys Ala Phe
            100                 105                 110

Gly Ala Met Ala Lys Pro Gly Leu Asn Asp Lys Leu Arg His Tyr Gly
        115                 120                 125

Ile Phe Asp Leu Glu Phe Arg Arg Val Arg Cys Lys Tyr Gln Gly Gly
    130                 135                 140

Gln Lys Ile Val Phe His Val Glu Lys Gly Ser Asn Pro Asn Tyr Leu
145                 150                 155                 160

Ala Met Leu Val Lys Phe Val Ala Asp Asp Gly Asp Ile Val Leu Met
                165                 170                 175

-continued

```
Glu Leu Lys Glu Lys Ser Ser Asp Trp Lys Pro Met Lys Leu Ser Trp
                180                 185                 190

Gly Ala Ile Trp Arg Met Asp Thr Pro Lys Ala Leu Val Pro Pro Phe
        195                 200                 205

Ser Ile Arg Leu Thr Ser Glu Ser Gly Lys Lys Val Ile Ala Gln Asp
    210                 215                 220

Val Ile Pro Val Asn Trp Lys Pro Asp Thr Tyr Asn Ser Asn Val
225                 230                 235                 240

Gln Phe

<210> SEQ ID NO 5
<211> LENGTH: 35
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 18
<223> OTHER INFORMATION: n is a or g
<220> FEATURE:
<221> NAME/KEY: misc_feature
<222> LOCATION: 27
<223> OTHER INFORMATION: n is a or g

<400> SEQUENCE: 5
gggcccccga aggtggcncc cggcaanaac atcac                              35

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 18
<223> OTHER INFORMATION: n is a, c, g, or t

<400> SEQUENCE: 6
gggcccccga aggtggcncc cggc                                          24

<210> SEQ ID NO 7
<211> LENGTH: 29
<212> TYPE: DNA
<213> ORGANISM: Artificial Sequence
<220> FEATURE:
<223> OTHER INFORMATION: Oligonucleotide

<400> SEQUENCE: 7
ggtgcctccc tcggtagtga ggcggacgg                                     29

<210> SEQ ID NO 8
<211> LENGTH: 26
<212> TYPE: DNA
<213> ORGANISM: Artificial Sequence
<220> FEATURE:
<223> OTHER INFORMATION: Oligonucleotide

<400> SEQUENCE: 8
cccttcttgg ccatggcgcc gaacgc                                        26

<210> SEQ ID NO 9
<211> LENGTH: 29
<212> TYPE: DNA
<213> ORGANISM: Artificial Sequence
```

```
<220> FEATURE:
<223> OTHER INFORMATION: Oligonucleotide

<400> SEQUENCE: 9
cggatcaagt gcatgcgcat gatgcatgg                                              29

<210> SEQ ID NO 10
<211> LENGTH: 34
<212> TYPE: DNA
<213> ORGANISM: Artificial Sequence
<220> FEATURE:
<223> OTHER INFORMATION: Oligonucleotide

<400> SEQUENCE: 10
gcttgcaagc ttctagaact ggacgttgga attg                                        34

<210> SEQ ID NO 11
<211> LENGTH: 35
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 18
<223> OTHER INFORMATION: n is a, c, g, or t

<400> SEQUENCE: 11
gggcccccga aggtggcncc cggcaaraac atcac                                       35

<210> SEQ ID NO 12
<211> LENGTH: 29
<212> TYPE: DNA
<213> ORGANISM: Artificial Sequence
<220> FEATURE:
<223> OTHER INFORMATION: Oligonucleotide

<400> SEQUENCE: 12
cggatcaagt gcatgcgcat gatgcatgg                                              29

<210> SEQ ID NO 13
<211> LENGTH: 30
<212> TYPE: DNA
<213> ORGANISM: Artificial Sequence
<220> FEATURE:
<223> OTHER INFORMATION: Oligonucleotide

<400> SEQUENCE: 13
gaaacaagtc gatctagaac tggacgttgg                                             30

<210> SEQ ID NO 14
<211> LENGTH: 39
<212> TYPE: DNA
<213> ORGANISM: Artificial Sequence
<220> FEATURE:
<223> OTHER INFORMATION: Oligonucleotide

<400> SEQUENCE: 14
tatattcata tgggccccccc caaggtgccg cccggcccc                                  39

<210> SEQ ID NO 15
<211> LENGTH: 34
<212> TYPE: DNA
<213> ORGANISM: Artificial Sequence
<220> FEATURE:
<223> OTHER INFORMATION: Oligonucleotide
```

<400> SEQUENCE: 15
gcttgcaagc ttctagaact ggacgttgga attg                                34

<210> SEQ ID NO 16
<211> LENGTH: 9
<212> TYPE: PRT
<213> ORGANISM: Artificial Sequence
<220> FEATURE:
<223> OTHER INFORMATION: Oligonucleotide

<400> SEQUENCE: 16

Gly Pro Pro Lys Val Ala Pro Gly Lys
1               5

<210> SEQ ID NO 17
<211> LENGTH: 12
<212> TYPE: PRT
<213> ORGANISM: Artificial Sequence
<220> FEATURE:
<223> OTHER INFORMATION: Oligonucleotide

<400> SEQUENCE: 17

Gly Pro Pro Lys Val Pro Pro Gly Pro Asn Ile Thr
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Oligonucleotide

<400> SEQUENCE: 18

Gly Pro Pro Lys Val Ala Pro Gly Lys Asn Ile Thr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Oligonucleotide

<400> SEQUENCE: 19

Gly Pro Pro Lys Val Pro Pro Gly Pro Asn Ile Thr
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Oligonucleotide

<400> SEQUENCE: 20

Ala Met Gly Asp Lys Pro Gly Pro Asn Ile Thr
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Oligonucleotide

<400> SEQUENCE: 21

```
Ile Ala Lys Val Pro Pro Gly Pro Asn Ile Thr
1               5                   10
```

<210> SEQ ID NO 22
<211> LENGTH: 11
<212> TYPE: PRT
<213> ORGANISM: Artificial Sequence
<220> FEATURE:
<223> OTHER INFORMATION: Oligonucleotide

<400> SEQUENCE: 22

```
Ile Pro Lys Val Pro Pro Gly Pro Asn Ile Thr
1               5                   10
```

<210> SEQ ID NO 23
<211> LENGTH: 243
<212> TYPE: PRT
<213> ORGANISM: Artificial sequence
<220> FEATURE:
<223> OTHER INFORMATION: Consensus sequence

<400> SEQUENCE: 23

```
Met Ser Ser Ser Val Leu Leu Val Val Ala Leu Ala Val Phe Gly Ala
1               5                   10                  15

Gly Ile Pro Lys Val Pro Pro Gly Pro Asn Ile Thr Ala Thr Tyr Gly
            20                  25                  30

Asp Lys Trp Leu Asp Ala Lys Ser Thr Trp Tyr Gly Lys Pro Thr Gly
        35                  40                  45

Ala Gly Pro Lys Asp Asn Gly Gly Ala Cys Gly Tyr Lys Asp Val Asp
    50                  55                  60

Lys Ala Pro Phe Gly Met Thr Gly Cys Gly Asn Thr Pro Ile Phe Lys
65                  70                  75                  80

Asp Gly Arg Gly Cys Gly Ser Cys Phe Glu Ile Lys Cys Lys Pro Glu
                85                  90                  95

Cys Ser Gly Glu Pro Val Thr Val His Ile Thr Asp Asp Asn Glu Glu
            100                 105                 110

Pro Ile Ala Pro Tyr His Phe Asp Leu Ser Gly Ala Phe Gly Ala Met
        115                 120                 125

Ala Lys Lys Gly Glu Glu Lys Leu Arg Ala Gly Glu Leu Glu Leu Gln
    130                 135                 140

Phe Arg Arg Val Lys Cys Lys Tyr Pro Gly Thr Lys Thr Phe His Val
145                 150                 155                 160

Glu Lys Gly Ser Asn Pro Asn Tyr Leu Ala Leu Leu Val Lys Tyr Val
                165                 170                 175

Gly Asp Gly Asp Val Val Ala Val Asp Ile Lys Glu Lys Gly Lys Asp
            180                 185                 190

Lys Trp Ile Leu Lys Glu Ser Trp Gly Ala Ile Trp Arg Asp Thr Pro
        195                 200                 205

Asp Lys Leu Thr Gly Pro Phe Thr Val Arg Tyr Thr Thr Glu Gly Gly
    210                 215                 220

Thr Lys Glu Ala Glu Asp Val Ile Pro Glu Gly Trp Lys Ala Asp Thr
225                 230                 235                 240

Tyr Ser Lys
```

<210> SEQ ID NO 24
<211> LENGTH: 263
<212> TYPE: PRT
<213> ORGANISM: Lolium pratense

<400> SEQUENCE: 24

Met Ala Ser Ser Ser Val Leu Leu Val Ala Leu Phe Ala Val
1               5                   10                  15

Phe Leu Gly Ser Ala His Gly Ile Ala Lys Val Pro Pro Gly Pro Asn
            20                  25                  30

Ile Thr Ala Glu Tyr Gly Asp Lys Trp Leu Asp Ala Lys Ser Thr Trp
        35                  40                  45

Tyr Gly Lys Pro Thr Gly Ala Gly Pro Lys Asp Asn Gly Gly Ala Cys
    50                  55                  60

Gly Tyr Lys Asn Val Asp Lys Ala Pro Phe Asn Gly Met Thr Gly Cys
65                  70                  75                  80

Gly Asn Thr Pro Ile Phe Lys Asp Gly Arg Gly Cys Gly Ser Cys Phe
                85                  90                  95

Glu Ile Lys Cys Thr Lys Pro Glu Ser Cys Ser Gly Glu Ala Val Thr
            100                 105                 110

Val Thr Ile Thr Asp Asp Asn Glu Glu Pro Ile Ala Pro Tyr His Phe
        115                 120                 125

Asp Leu Ser Gly His Ala Phe Gly Ser Met Ala Lys Lys Gly Glu Glu
    130                 135                 140

Gln Asn Val Arg Ser Ala Gly Glu Leu Glu Leu Gln Phe Arg Arg Val
145                 150                 155                 160

Lys Cys Lys Tyr Pro Asp Asp Thr Lys Pro Thr Phe His Val Glu Lys
                165                 170                 175

Ala Ser Asn Pro Asn Tyr Leu Ala Ile Leu Val Lys Tyr Val Asp Gly
            180                 185                 190

Asp Gly Asp Val Val Ala Val Asp Ile Lys Glu Lys Gly Lys Asp Lys
        195                 200                 205

Trp Ile Glu Leu Lys Glu Ser Trp Gly Ala Val Trp Arg Ile Asp Thr
    210                 215                 220

Pro Asp Lys Leu Thr Gly Pro Phe Thr Val Arg Tyr Thr Thr Glu Gly
225                 230                 235                 240

Gly Thr Lys Ser Glu Phe Glu Asp Val Ile Pro Glu Gly Trp Lys Ala
                245                 250                 255

Asp Thr Ser Tyr Ser Ala Lys
            260

<210> SEQ ID NO 25
<211> LENGTH: 269
<212> TYPE: PRT
<213> ORGANISM: Phalaris arundinacea

<400> SEQUENCE: 25

Met Met Lys Met Val Cys Ser Ser Ser Ser Ser Leu Leu Val Val
1               5                   10                  15

Ala Ala Leu Leu Ala Val Phe Val Gly Ser Ala Gln Gly Ile Ala Lys
            20                  25                  30

Val Pro Pro Gly Pro Asn Ile Thr Ala Glu Tyr Gly Asp Lys Trp Leu
        35                  40                  45

Asp Ala Lys Ser Thr Trp Tyr Gly Lys Pro Thr Gly Ala Gly Pro Lys
    50                  55                  60

Asp Asn Gly Gly Ala Cys Gly Tyr Lys Asp Val Asp Lys Ala Pro Phe
65                  70                  75                  80

Asn Gly Met Thr Gly Cys Gly Asn Thr Pro Ile Phe Lys Asp Gly Arg
                85                  90                  95

```
Gly Cys Gly Ser Cys Phe Glu Leu Lys Cys Ser Lys Pro Glu Ser Cys
            100                 105                 110

Ser Gly Glu Pro Ile Thr Val His Ile Thr Asp Asp Asn Glu Glu Pro
        115                 120                 125

Ile Ala Pro Tyr His Phe Asp Leu Ser Gly His Ala Phe Gly Ser Met
130                 135                 140

Ala Lys Lys Gly Glu Glu Asn Val Arg Gly Ala Gly Glu Leu Glu
145                 150                 155                 160

Leu Gln Phe Arg Arg Val Lys Cys Lys Tyr Pro Asp Gly Thr Lys Pro
                165                 170                 175

Thr Phe His Val Glu Lys Gly Ser Asn Pro Asn Tyr Leu Ala Leu Leu
            180                 185                 190

Val Lys Tyr Val Asp Gly Asp Gly Asp Val Val Ala Val Asp Ile Lys
        195                 200                 205

Glu Lys Gly Lys Asp Lys Trp Ile Glu Leu Lys Glu Ser Trp Gly Ala
    210                 215                 220

Ile Trp Arg Ile Asp Thr Pro Asp Lys Leu Thr Gly Pro Phe Thr Val
225                 230                 235                 240

Arg Tyr Thr Thr Glu Gly Gly Thr Lys Ala Glu Phe Glu Asp Val Ile
                245                 250                 255

Pro Glu Gly Trp Lys Ala Asp Thr His Asp Ala Ser Lys
            260                 265

<210> SEQ ID NO 26
<211> LENGTH: 265
<212> TYPE: PRT
<213> ORGANISM: Holcus lanatus

<400> SEQUENCE: 26

Met Ala Ser Ser Ser Arg Ser Val Leu Leu Leu Val Ala Ala Leu Phe
1               5                   10                  15

Ala Val Phe Leu Gly Ser Ala His Gly Ile Ala Lys Val Pro Pro Gly
            20                  25                  30

Pro Asn Ile Thr Ala Thr Tyr Gly Asp Glu Trp Leu Asp Ala Lys Ser
        35                  40                  45

Thr Trp Tyr Gly Lys Pro Thr Gly Ala Gly Pro Lys Asp Asn Gly Gly
    50                  55                  60

Ala Cys Gly Tyr Lys Asp Val Asp Lys Pro Pro Phe Ser Gly Met Thr
65                  70                  75                  80

Gly Cys Gly Asn Thr Pro Ile Phe Lys Asp Gly Arg Gly Cys Gly Ser
                85                  90                  95

Cys Phe Glu Ile Lys Cys Thr Lys Pro Glu Ser Cys Ser Gly Glu Pro
            100                 105                 110

Val Thr Val His Ile Thr Asp Asp Asn Glu Glu Pro Ile Ala Pro Tyr
        115                 120                 125

His Phe Asp Leu Ser Gly His Ala Phe Gly Ser Met Ala Lys Lys Gly
    130                 135                 140

Glu Glu Gln Lys Leu Arg Ser Ala Gly Glu Leu Glu Leu Lys Phe Arg
145                 150                 155                 160

Arg Val Lys Cys Lys Tyr Pro Asp Gly Thr Lys Pro Thr Phe His Val
                165                 170                 175

Glu Lys Gly Ser Asn Pro Asn Tyr Leu Ala Leu Leu Val Lys Tyr Ile
            180                 185                 190

Asp Gly Asp Gly Asp Val Val Ala Val Asp Ile Lys Glu Lys Gly Lys
        195                 200                 205
```

```
Asp Lys Trp Ile Glu Leu Lys Glu Ser Trp Gly Ala Val Trp Arg Val
    210                 215                 220

Asp Thr Pro Asp Lys Leu Thr Gly Pro Phe Thr Val Arg Tyr Thr Thr
225                 230                 235                 240

Glu Gly Gly Thr Lys Gly Glu Ala Glu Asp Val Ile Pro Glu Gly Trp
                245                 250                 255

Lys Ala Asp Thr Ala Tyr Glu Ala Lys
            260                 265
```

<210> SEQ ID NO 27
<211> LENGTH: 265
<212> TYPE: PRT
<213> ORGANISM: Dactylis glomerata

<400> SEQUENCE: 27

```
Met Ala Ser Ser Arg Ser Val Leu Leu Val Ala Ala Leu Phe
1               5                   10                  15

Ala Val Phe Leu Gly Ser Ala His Gly Ile Ala Lys Val Pro Pro Gly
                20                  25                  30

Pro Asn Ile Thr Ala Thr Tyr Gly Asp Glu Trp Leu Asp Ala Lys Ser
            35                  40                  45

Thr Trp Tyr Gly Lys Pro Thr Gly Ala Gly Pro Lys Asp Asn Gly Gly
    50                  55                  60

Ala Cys Gly Tyr Lys Asp Val Asp Lys Pro Pro Phe Ser Gly Met Thr
65                  70                  75                  80

Gly Cys Gly Asn Thr Pro Ile Phe Lys Asp Gly Arg Gly Cys Gly Ser
                85                  90                  95

Cys Phe Glu Ile Lys Cys Thr Lys Pro Glu Ser Cys Ser Gly Glu Pro
            100                 105                 110

Val Thr Val His Ile Thr Asp Asp Asn Glu Glu Pro Ile Ala Pro Tyr
        115                 120                 125

His Phe Asp Leu Ser Gly His Ala Phe Gly Ser Met Ala Lys Lys Gly
    130                 135                 140

Glu Glu Gln Lys Leu Arg Ser Ala Gly Glu Leu Glu Leu Lys Phe Arg
145                 150                 155                 160

Arg Val Lys Cys Lys Tyr Pro Asp Gly Thr Lys Pro Thr Phe His Val
                165                 170                 175

Glu Lys Gly Ser Asn Pro Asn Tyr Leu Ala Leu Leu Val Lys Tyr Ile
            180                 185                 190

Asp Gly Asp Gly Asp Val Val Ala Val Asp Ile Lys Glu Lys Gly Lys
        195                 200                 205

Asp Lys Trp Ile Glu Leu Lys Glu Ser Trp Gly Ala Val Trp Arg Val
    210                 215                 220

Asp Thr Pro Asp Lys Leu Thr Gly Pro Phe Thr Val Arg Tyr Thr Thr
225                 230                 235                 240

Glu Gly Gly Thr Lys Gly Glu Ala Glu Asp Val Ile Pro Glu Gly Trp
                245                 250                 255

Lys Ala Asp Thr Ala Tyr Glu Ala Lys
            260                 265
```

<210> SEQ ID NO 28
<211> LENGTH: 263
<212> TYPE: PRT
<213> ORGANISM: Phleum pratense

<400> SEQUENCE: 28

```
Met Ala Ser Ser Ser Val Leu Leu Val Val Leu Phe Ala Val
1               5                   10                  15

Phe Leu Gly Ser Ala Tyr Gly Ile Pro Lys Val Pro Gly Pro Asn
                20                  25                  30

Ile Thr Ala Thr Tyr Gly Asp Lys Trp Leu Asp Ala Lys Ser Thr Trp
            35                  40                  45

Tyr Gly Lys Pro Thr Gly Ala Gly Pro Lys Asp Asn Gly Gly Ala Cys
50                      55                  60

Gly Tyr Lys Asp Val Asp Lys Pro Pro Phe Ser Gly Met Thr Gly Cys
65                  70                  75                  80

Gly Asn Thr Pro Ile Phe Lys Ser Gly Arg Gly Cys Gly Ser Cys Phe
                85                  90                  95

Glu Ile Lys Cys Thr Lys Pro Glu Ala Cys Ser Gly Glu Pro Val Val
                100                 105                 110

Val His Ile Thr Asp Asp Asn Glu Glu Pro Ile Ala Pro Tyr His Phe
            115                 120                 125

Asp Leu Ser Gly His Ala Phe Gly Ala Met Ala Lys Lys Gly Asp Glu
        130                 135                 140

Gln Lys Leu Arg Ser Ala Gly Glu Leu Glu Leu Gln Phe Arg Arg Val
145                 150                 155                 160

Lys Cys Lys Tyr Pro Glu Gly Thr Lys Val Thr Phe His Val Glu Lys
                165                 170                 175

Gly Ser Asn Pro Asn Tyr Leu Ala Leu Leu Val Lys Tyr Val Asn Gly
            180                 185                 190

Asp Gly Asp Val Ala Val Asp Ile Lys Glu Lys Gly Lys Asp Lys
                195                 200                 205

Trp Ile Glu Leu Lys Glu Ser Trp Gly Ala Ile Trp Arg Ile Asp Thr
210                 215                 220

Pro Asp Lys Leu Thr Gly Pro Phe Thr Val Arg Tyr Thr Thr Glu Gly
225                 230                 235                 240

Gly Thr Lys Thr Glu Ala Glu Asp Val Ile Pro Glu Gly Trp Lys Ala
                245                 250                 255

Asp Thr Ser Tyr Glu Ser Lys
                260

<210> SEQ ID NO 29
<211> LENGTH: 263
<212> TYPE: PRT
<213> ORGANISM: Poa pratensis

<400> SEQUENCE: 29

Met Ala Ser Ser Ser Val Leu Leu Val Val Ala Leu Phe Ala Val
1               5                   10                  15

Phe Leu Gly Thr Ala His Gly Ile Ala Lys Val Pro Gly Pro Asn
                20                  25                  30

Ile Thr Ala Thr Tyr Gly Asp Lys Trp Leu Asp Ala Lys Ser Thr Trp
            35                  40                  45

Tyr Gly Lys Pro Thr Gly Ala Gly Pro Lys Asp Asn Gly Gly Ala Cys
50                      55                  60

Gly Tyr Lys Asp Val Asp Lys Ala Pro Phe Ser Gly Met Thr Gly Cys
65                  70                  75                  80

Gly Asn Thr Pro Ile Phe Lys Ser Gly Arg Gly Cys Gly Ser Cys Phe
                85                  90                  95

Glu Ile Lys Cys Thr Lys Pro Glu Ser Cys Ser Gly Glu Pro Val Leu
```

```
                100                 105                 110
Val His Ile Thr Asp Asp Asn Glu Glu Pro Ile Ala Ala Tyr His Phe
            115                 120                 125
Asp Leu Ser Gly Lys Ala Phe Gly Ala Met Ala Lys Lys Gly Glu Glu
        130                 135                 140
Gln Lys Leu Arg Ser Ala Gly Glu Leu Glu Leu Lys Phe Arg Arg Val
145                 150                 155                 160
Lys Cys Glu Tyr Pro Glu Gly Thr Lys Val Thr Phe His Val Glu Lys
                165                 170                 175
Gly Ser Asn Pro Asn Tyr Leu Ala Leu Leu Val Lys Tyr Val Thr Gly
            180                 185                 190
Asp Gly Asp Val Val Ala Val Asp Ile Lys Glu Lys Gly Lys Asp Lys
        195                 200                 205
Trp Ile Glu Leu Lys Glu Ser Trp Gly Ser Ile Trp Arg Val Asp Thr
210                 215                 220
Pro Asp Lys Leu Thr Gly Pro Phe Thr Val Arg Tyr Thr Thr Glu Gly
225                 230                 235                 240
Gly Thr Lys Gly Glu Ala Glu Asp Val Ile Pro Glu Gly Trp Lys Ala
                245                 250                 255
Asp Thr Ala Tyr Ala Ser Lys
            260

<210> SEQ ID NO 30
<211> LENGTH: 261
<212> TYPE: PRT
<213> ORGANISM: Sorghum halepense

<400> SEQUENCE: 30

Met Ser Trp Ser Met Gln Val Ala Leu Val Val Ala Leu Ala Phe Leu
1               5                   10                  15
Val Gly Gly Ala Trp Cys Gly Pro Lys Val Ala Pro Gly Lys Asn
            20                  25                  30
Ile Thr Ala Thr Tyr Gly Ser Asp Trp Leu Glu Arg Lys Ala Thr Trp
        35                  40                  45
Tyr Gly Lys Pro Thr Gly Ala Gly Pro Asp Asp Asn Gly Gly Ala Cys
    50                  55                  60
Gly Tyr Lys Asp Val Asn Lys Ala Pro Phe Asn Ser Met Gly Ala Cys
65                  70                  75                  80
Gly Asn Leu Pro Ile Phe Lys Asp Gly Leu Gly Cys Gly Ser Cys Phe
                85                  90                  95
Glu Ile Lys Cys Asp Lys Pro Ala Glu Cys Ser Gly Glu Ala Val Val
            100                 105                 110
Val His Ile Thr Asp Met Asn Tyr Glu Gln Ile Ala Ala Tyr His Phe
        115                 120                 125
Asp Leu Ala Gly Thr Ala Phe Gly Ala Met Ala Lys Lys Gly Glu Glu
    130                 135                 140
Glu Lys Leu Arg Lys Ala Gly Ile Ile Asp Met Lys Phe Arg Arg Val
145                 150                 155                 160
Lys Cys Lys Tyr Gly Glu Lys Val Thr Phe His Val Glu Lys Gly Ser
                165                 170                 175
Asn Pro Asn Tyr Leu Ala Leu Leu Val Lys Tyr Val Asp Gly Asp Gly
            180                 185                 190
Asp Val Val Gly Val Asp Ile Lys Glu Lys Gly Gly Asp Ala Tyr Gln
        195                 200                 205
```

```
Pro Leu Lys His Ser Trp Gly Ala Ile Trp Arg Lys Asp Ser Asp Lys
    210                 215                 220
Pro Ile Lys Phe Pro Val Thr Val Gln Ile Thr Thr Glu Gly Gly Thr
225                 230                 235                 240
Lys Thr Ala Tyr Glu Asp Val Ile Pro Glu Gly Trp Lys Ala Asp Thr
                245                 250                 255
Thr Tyr Thr Ala Lys
            260
```

<210> SEQ ID NO 31
<211> LENGTH: 267
<212> TYPE: PRT
<213> ORGANISM: Oryza sativa

<400> SEQUENCE: 31

```
Met Ala Ser Ser Ser Leu Leu Ala Cys Val Val Ala Ala Met
1               5                   10                  15
Val Ser Ala Val Ser Cys Gly Pro Pro Lys Val Pro Pro Gly Pro Asn
                20                  25                  30
Ile Thr Thr Ser Tyr Gly Asp Lys Trp Leu Glu Ala Lys Ala Thr Trp
                35                  40                  45
Tyr Gly Ala Pro Lys Gly Ala Gly Pro Lys Asp Asn Gly Gly Ala Cys
50                  55                  60
Gly Tyr Lys Asp Val Asp Lys Ala Pro Phe Leu Gly Met Asn Ser Cys
65                  70                  75                  80
Gly Asn Asp Pro Ile Phe Lys Asp Gly Lys Gly Cys Gly Ser Cys Phe
                85                  90                  95
Glu Ile Lys Cys Ser Lys Pro Glu Ala Cys Ser Asp Lys Pro Ala Leu
                100                 105                 110
Ile His Val Thr Asp Met Asn Asp Glu Pro Ile Ala Ala Tyr His Phe
                115                 120                 125
Asp Leu Ser Gly Leu Ala Phe Gly Ala Met Ala Lys Asp Gly Lys Asp
            130                 135                 140
Glu Glu Leu Arg Lys Ala Gly Ile Ile Asp Thr Gln Phe Arg Arg Val
145                 150                 155                 160
Lys Cys Lys Tyr Pro Ala Asp Thr Lys Ile Thr Phe His Ile Glu Lys
                165                 170                 175
Ala Ser Asn Pro Asn Tyr Leu Ala Leu Leu Val Lys Tyr Val Ala Gly
                180                 185                 190
Asp Gly Asp Val Val Glu Val Glu Ile Lys Glu Lys Gly Ser Glu Glu
            195                 200                 205
Trp Lys Ala Leu Lys Glu Ser Trp Gly Ala Ile Trp Arg Ile Asp Thr
    210                 215                 220
Pro Lys Pro Leu Lys Gly Pro Phe Ser Val Arg Val Thr Thr Glu Gly
225                 230                 235                 240
Gly Glu Lys Ile Ile Ala Glu Asp Ala Ile Pro Asp Gly Trp Lys Ala
                245                 250                 255
Asp Ser Val Tyr Lys Ser Asn Val Gln Ala Lys
                260                 265
```

<210> SEQ ID NO 32
<211> LENGTH: 262
<212> TYPE: PRT
<213> ORGANISM: Cynodon dactylon

<400> SEQUENCE: 32

Met Leu Ala Ala Val Ala Val Leu Ala Ser Met Val Gly Gly Ala
1               5                   10                  15

Trp Cys Ala Met Gly Asp Lys Pro Gly Pro Asn Ile Thr Ala Thr Tyr
            20                  25                  30

Gly Asp Lys Trp Leu Asp Ala Lys Ala Thr Phe Tyr Gly Ser Asp Pro
        35                  40                  45

Arg Gly Ala Ala Pro Asp Asp His Gly Gly Ala Cys Gly Tyr Lys Asp
50                  55                  60

Val Asp Lys Ala Pro Phe Asp Gly Met Thr Gly Cys Gly Asn Glu Pro
65                  70                  75                  80

Ile Phe Lys Asp Gly Leu Gly Cys Gly Ser Cys Tyr Glu Ile Lys Cys
                85                  90                  95

Lys Glu Pro Ala Glu Cys Ser Gly Glu Pro Val Leu Ile Lys Ile Thr
            100                 105                 110

Asp Lys Asn Tyr Glu His Ile Ala Ala Tyr His Phe Asp Leu Ser Gly
        115                 120                 125

Lys Ala Phe Gly Ala Met Ala Lys Lys Gly Glu Glu Asp Lys Leu Arg
130                 135                 140

Lys Ala Gly Glu Leu Met Leu Gln Phe Arg Arg Val Lys Cys Glu Tyr
145                 150                 155                 160

Pro Ser Asp Thr Lys Ile Thr Phe His Val Glu Lys Gly Ser Ser Pro
                165                 170                 175

Asn Tyr Leu Ala Leu Leu Val Lys Tyr Ala Ala Gly Asp Gly Asn Ile
            180                 185                 190

Val Gly Val Asp Ile Lys Pro Lys Gly Ser Asp Val Phe Leu Pro Met
        195                 200                 205

Lys Leu Ser Trp Gly Ala Ile Trp Arg Met Asp Pro Pro Lys Pro Leu
210                 215                 220

Lys Gly Pro Phe Thr Ile Arg Leu Thr Ser Glu Ser Gly Gly His Val
225                 230                 235                 240

Glu Gln Glu Asp Val Ile Pro Glu Asp Trp Lys Pro Asp Thr Val Tyr
                245                 250                 255

Lys Ser Lys Ile Gln Phe
            260

<210> SEQ ID NO 33
<211> LENGTH: 269
<212> TYPE: PRT
<213> ORGANISM: Zea mays

<400> SEQUENCE: 33

Met Gly Ser Leu Ala Asn Asn Ile Met Val Val Gly Ala Val Leu Ala
1               5                   10                  15

Ala Leu Val Val Gly Gly Ser Cys Gly Pro Pro Lys Val Pro Pro Gly
            20                  25                  30

Pro Asn Ile Thr Thr Asn Tyr Asn Gly Lys Trp Leu Thr Ala Arg Ala
        35                  40                  45

Thr Trp Tyr Gly Gln Pro Asn Gly Ala Gly Ala Pro Asp Asn Gly Gly
    50                  55                  60

Ala Cys Gly Ile Lys Asn Val Asn Leu Pro Pro Tyr Ser Gly Met Thr
65                  70                  75                  80

Ala Cys Gly Asn Val Pro Ile Phe Lys Asp Gly Lys Gly Cys Gly Ser
                85                  90                  95

Cys Tyr Glu Val Arg Cys Lys Glu Lys Pro Glu Cys Ser Gly Asn Pro
            100                 105                 110

```
Val Thr Val Phe Ile Thr Asp Met Asn Tyr Glu Pro Ile Ala Pro Tyr
        115             120             125
His Phe Asp Leu Ser Gly Lys Ala Phe Gly Ser Leu Ala Lys Pro Gly
    130             135             140
Leu Asn Asp Lys Leu Arg His Cys Gly Ile Met Asp Val Glu Phe Arg
145             150             155             160
Arg Val Arg Cys Lys Tyr Pro Ala Gly Gln Lys Ile Val Phe His Ile
            165             170             175
Glu Lys Gly Cys Asn Pro Asn Tyr Val Ala Val Leu Val Lys Phe Val
        180             185             190
Ala Asp Asp Gly Asp Ile Val Leu Met Glu Ile Gln Asp Lys Leu Ser
    195             200             205
Ala Glu Trp Lys Pro Met Lys Leu Ser Trp Gly Ala Ile Trp Arg Met
    210             215             220
Asp Thr Ala Lys Ala Leu Lys Gly Pro Phe Ser Ile Arg Leu Thr Ser
225             230             235             240
Glu Ser Gly Lys Lys Val Ile Ala Lys Asp Ile Ile Pro Ala Asn Trp
            245             250             255
Arg Pro Asp Ala Val Tyr Thr Ser Asn Val Gln Phe Tyr
        260             265
```